United States Patent
Hawley et al.

(10) Patent No.: US 6,846,828 B2
(45) Date of Patent: Jan. 25, 2005

(54) AMINOPYRIMIDINE AND AMINOPYRIDINE ANTI-INFLAMMATION AGENTS

(75) Inventors: Ronald Charles Hawley, Mountain View, CA (US); Sharada Shenvi Labadie, Sunnyvale, CA (US); Eric Brian Sjogren, Mountain View, CA (US); Francisco Xavier Talamas, Mountain View, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 275 days.

(21) Appl. No.: 10/288,968

(22) Filed: Nov. 6, 2002

(65) Prior Publication Data

US 2003/0144303 A1 Jul. 31, 2003

Related U.S. Application Data

(60) Provisional application No. 60/338,312, filed on Nov. 7, 2001.

(51) Int. Cl.[7] .................... A61K 31/505; A61K 31/506; C07D 239/32; C07D 403/04
(52) U.S. Cl. ........................ 514/256; 514/275; 514/340; 514/341; 514/342; 514/351; 514/352; 544/316; 544/319; 544/326; 544/327; 544/328; 544/329; 544/331; 544/332; 546/270.4; 546/272.4; 546/274.1; 546/300; 546/312
(58) Field of Search ................................ 544/316, 319, 544/326, 327, 328, 329, 331, 332; 546/270.4, 272.4, 274.1, 300, 312; 514/256, 275, 340, 341, 342, 351, 352

(56) References Cited

U.S. PATENT DOCUMENTS

2002/0161004 A1  10/2002  Browner et al. ......... 514/228.2

FOREIGN PATENT DOCUMENTS

EP  0 457 717 A1  11/1991
WO  WO 01/56553 A2  8/2001

OTHER PUBLICATIONS

Hellmut Breder, "Synthesen heterocyclischer Aldehyde. Pyrimidinaldehyd–(4)," Chemische Berichte, 1964, pp 3407–3417, vol. 97:12.

Iris Hall, "The Anti–inflammatory Activity of Metal Complexes of Heterocyclic Thiosemicarbazones, 2–Substituted Pyridine N–Oxides and 2–Pyridylthioureas," Applied Organometallic Chemistry, 1996, pp 485–493, vol. 10:7.

*Primary Examiner*—Richard L. Raymond
(74) *Attorney, Agent, or Firm*—Grant D. Green

(57) ABSTRACT

Aminopyrimidine and aminopyridine (I) compounds, compositions and methods useful in the treatment of inflammatory, metabolic or malignant conditions, are provided herein.

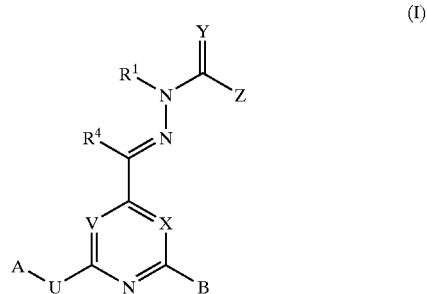

(I)

51 Claims, No Drawings

AMINOPYRIMIDINE AND AMINOPYRIDINE ANTI-INFLAMMATION AGENTS

CROSS-REFERENCES TO RELATED APPLICATIONS

The present invention claims the priority benefit under Title 35 U.S.C. 119(e) of U.S. Provisional Application Ser. No. 60/338,312, filed Nov. 7, 2001, the disclosure of which is herein incorporated by reference This application incorporates by reference the disclosure of pending U.S. patent application Ser. No. 10/004,287, filed Oct. 23, 2001, titled "Anti-inflammation Agents," inventors Michelle F. Browner, et al.

BACKGROUND OF THE INVENTION

Tumor Necrosis Factor (TNF) and Interleukin-1 (IL-1) are cytokines that have been implicated in a wide range of biological processes, including inflammation. The recruitment of immune cells to sites of injury involves the concerted interactions of a large number of soluble mediators. Several cytokines appear to play key roles in these processes, particularly IL-1 and TNF. Both cytokines are derived from mononuclear cells and macrophages, along with other cell types. Physiologically, they produce many of the same proinflammatory responses, including fever, sleep and anorexia, mobilization and activation of polymorphonuclear leukocytes, induction of cyclooxygenase and lipoxygenase enzymes, increase in adhesion molecule expression, activation of B-cells, T-cells and natural killer cells, and stimulation of production of other cytokines. Other actions include a contribution to the tissue degeneration seen in chronic inflammatory conditions, such as stimulation of fibroblast proliferation, induction of collagenase, etc. They have also been implicated in the process of bone resorption and adipose tissue regulation. Thus, these cytokines play key roles in a large number of pathological conditions, including rheumatoid arthritis, inflammatory bowel disease, diabetes, obesity, bone mass loss, cancer, neurological conditions such as ischemic stroke or closed head injuries, etc.

Cytokines trigger a variety of changes in gene expression in their target cells by binding and activating their respective cognate receptors, which sets in motion certain biochemical events, including the activation of otherwise latent transcription factors. Members of the NF-kB Rel family of transcription factors represent some of the most prominent of these transcription factors, having been implicated in the regulation of genes involved in inflammation, cell proliferation, apoptosis, and several other basic cellular functions (I. M. Verma et al, *Genes Dev.* 9, 2723 (1995); Baichwal & Baeuerle, *Curr. Biol.* 7, 94 (1997)).

The best studied member of this family of transcription factors is NF-kB, which generally exists in cells as a heterodimer of two proteins: p50 (NF-kB1) and p65 (RelA), although homodimers of these individual components are also possible (Baeuerle and Baltimore, *Cell*, 53, 211 (1988); Baeuerle and Henkel, *Annu. Rev. Immunol.*, 12, 141 (1994)). NF-kB, in its inactive form, resides in the cytoplasm of cells, but migrates to the nucleus in response to various types of stimuli, such as pro-inflammatory cytokines (e.g., TNF and IL-1), ultraviolet irradiation and viral infection (Verma, 1995; Baichwal, 1997; Cao et al, *Science*, 271, 1128 (1996)). TNF and IL-1 have been shown to be two key pro-inflammation agents in a wide variety of pathological conditions, including rheumatoid arthritis, septic shock, inflammatory bowel disease, dermal sensitization disorders, neurological trauma such as stroke or closed-head injuries, etc.

In its inactive state, the NF-kB heterodimer is held in the cytoplasm by association with inhibitory IkB proteins. Recently, the three-dimensional structure of a NF-kB/IkB ternary complex has been solved (Huxford et al, *Cell*, 95, 759 (1998); Jacobs et al, *Cell*, 95, 749 (1998)). When cells are treated with the appropriate stimuli, such as IL-1 or TNF, intracellular signal transduction pathways are activated that lead to the eventual phosphorylation of IkB proteins on two specific residues (serines 32 and 36 in IkB-alpha, serines 19 and 23 in IkB-beta). Mutation of one or both of these serine residues renders IkB resistant to cytokine-induced phosphorylation. This signal-induced phosphorylation targets IkB for ubiquitination and proteosome-mediated degradation, allowing nuclear translocation of NF-kB (Thanos and Maniatis, *Cell*, 80, 529 (1995)). The only regulated step in the IkB degradation pathway is the phosphorylation of IkB by IkB kinases (IKK) (Yaron et al, *EMBO J.* 16, 6486 (1997)).

Several intermediate steps in the TNF- and IL-1-activated signaling pathways that result in IkB phosphorylation have been elucidated in recent years. The protein kinases MEKK1 and MLK3 have been implicated in the induction of IKK activity (Malinin et al, *Nature*, 385, 540 (1997); Song et al, *Proc. Natl. Acad. Sci. USA*, 94, 9792 (1997); Lee et al, *Proc. Natl. Acad. Sci. USA*. 95, 9319 (1998); Hehner et al, *Mol. Cell. Biol.* 20, 2556 (2000); Wang et al, *Nature*, 412, 346 (2001)). While the specific details remain somewhat unclear regarding how these or other intermediate proteins may interact with and/or stimulate IKK activity in cells, significant progress has been made in elucidating the enzymes responsible for IkB phosphorylation. Two IKK enzymes, generally referred to as either IKK-alpha and IKK-beta (Woronicz et al, *Science*, 278, 866 (1997); Zandi et al, *Cell*, 91, 243 (1997)) or IKK-1 and IKK-2 (Mercurio et al, *Science*, 278, 860 (1997)) have been discovered. Both forms of IKK can exist as homodimers and as IKK-alpha/IKK-beta heterodimers. Another recently discovered component of the IkB kinase complex is a regulatory protein, known as IKK-gamma or NF-κB-Essential Modulator (NEMO) (Rothwarf et al, *Nature*, 395, 297 (1998)). NEMO does not contain a catalytic domain, and thus it appears to have no direct kinase activity and it probably serves a regulatory function. Existing data suggest that the predominant form of IKK in cells is an IKK-alpha/IKK-beta heterodimer associated with either a dimer or a trimer of NEMO (Rothwarf et al, *Nature* 395, 297 (1998)).

Biochemical and molecular biology experiments have clearly identified IKK-alpha and IKK-beta as the most likely mediators of TNF- and IL-1-induced IkB phosphorylation and degradation, which results in NF-kB activation and upregulation of families of genes involved in inflammatory processes (Woronicz et al, *Science* (1997); Karin, *Oncogene* 18, 6867 (1999); Karin, *J. Biol. Chem.* 274, 27339 (1999)). IKK-alpha and IKK-beta have very similar primary structures, displaying more than 50% overall sequence identity. In the kinase domain, their sequences are 65% identical.

Based on our present understanding of the critical role played by TNF and IL-1 in the wide array of pathological conditions described above, and the involvement of IKK-alpha and IKK-beta in the signal transduction of both cytokines, the discovery of compounds that potently and selectively inhibit either of these kinases would result in a major advancement in the therapy of those conditions. In this application we describe a novel type of compounds which display such desirable activity profile.

SUMMARY OF THE INVENTION

In one aspect, the present invention provides compounds useful in the treatment of inflammatory, metabolic or malignant conditions, having the formula:

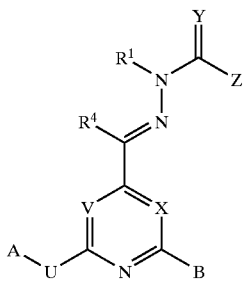

(I)

In Formula (I):

One of either V or X is N and the other is —$CR_a$, or both V and X are —$CR_a$ (where each $R_a$ is independently hydrogen, alkyl, cycloalkyl or cycloalkylalkyl;

Y represents O, S or N(R), wherein R is H, CN, $NO_2$, $(C_1-C_{10})$alkyl, $(C_3-C_7)$cycloalkyl, $(C_3-C_7)$cycloalkyl-alkyl, $(C_3-C_{10})$alkenyl or $(C_2-C_{10})$alkynyl;

Z represents H, $(C_1-C_6)$alkyl, $(C_3-C_7)$cycloalkyl, $(C_3-C_7)$cycloalkyl-alkyl, $(C_2-C_6)$alkenyl, $(C_2-C_6)$alkynyl, aryl or $N(R^2)(R^3)$;

$R^1$ represents H, $(C_1-C_{10})$alkyl, $(C_3-C_{10})$alkenyl, $(C_2-C_{10})$alkynyl, $(C_3-C_7)$cycloalkyl, $(C_3-C_7)$cycloalkyl-alkyl, $(C_1-C_{10})$heteroalkyl, heterocyclyl, heterocyclylalkyl, aryl, aryl$(C_1-C_4)$alkyl, aryl$(C_1-C_4)$heteroalkyl, heteroaryl $(C_1-C_4)$alkyl, heteroaryl$(C_1-C_4)$heteroalkyl, —$C(O)R^{11}$ or alkylene-$C(O)R^{11}$;

$R^{11}$ is hydrogen, $(C_1-C_6)$alkyl or $NR^{12}R^{13}$ (where $R^{12}$ and $R^{13}$ are independently hydrogen, $(C_1-C_6)$alkyl or heteroalkyl);

$R^2$ and $R^3$ are each independently H, $(C_1-C_{10})$alkyl, $(C_3-C_{10})$alkenyl, $(C_2-C_{10})$alkynyl, $(C_3-C_7)$cycloalkyl, $(C_3-C_7)$cycloalkyl-alkyl, or $(C_1-C_{10})$heteroalkyl, or $R^2$ and $R^3$ can be combined to form a 5–7-membered heterocyclyl ring;

$R^4$ represents H, alkyl, $(C_3-C_7)$cycloalkyl, $(C_3-C_7)$ cycloalkyl-alkyl, $(C_2-C_6)$alkenyl or $(C_2-C_6)$alkynyl;

A represents H, $(C_1-C_{10})$alkyl, $(C_3-C_{10})$alkenyl, $(C_2-C_{10})$alkynyl, $(C_1-C_6)$ haloalkyl, $(C_3-C_7)$cycloalkyl, $(C_3-C_7)$cycloalkyl-alkyl, $(C_1-C_{10})$heteroalkyl,heterocyclyl, heterocyclylalkyl, heterosubstituted cycloalkyl, aryl, aryl $(C_1-C_4)$alkyl, aryl$(C_1-C_4)$heteroalkyl, heteroaryl, heteroaryl$(C_1-C_4)$alkyl heteroaryl$(C_1-C_4)$heteroalkyl or $R^aR^bNC(=X)$— wherein $R^a$ and $R^b$ are independently hydrogen, $(C_1-C_4)$ alkyl or aryl and X is O or S;

B represents a substituted or unsubstituted five- or six-membered aromatic ring containing at least one nitrogen atom, and from 0 to 3 additional heteroatoms, wherein the B ring substituents are selected from halogen, $CF_3$, $CF_3O$, $(C_1-C_6)$alkyl, amino, $(C_1-C_6)$alkylamino, di$(C_1-C_6)$ alkylamino, cyano, nitro, sulfonamido, acyl, acylamino, and carboxamido; and U represents $NR^5$, O or S, wherein $R^5$ is H or $(C_1-C_6)$ alkyl.

In another aspect, the present invention provides pharmaceutical compositions comprising one or more compounds of formula I in admixture with a pharmaceutically acceptable excipient.

In another aspect, this invention provides processes for the preparing compounds of Formula (I).

In yet another aspect, the present invention provides methods for the treatment of an inflammatory, metabolic or malignant condition, comprising administering to a subject in need of such treatment a compound of formula I.

DETAILED DESCRIPTION OF THE INVENTION

Abbreviations and Definitions

Unless otherwise stated, the following terms used in the specification and claims have the meanings given below:

"Acyl" means the group —C(O)R', where R' is hydrogen, alkyl, cycloalkyl, cycloalkyl-alkyl, aryl and aryl-alkyl.

"Alkyl" means a linear saturated monovalent hydrocarbon radical or a branched saturated monovalent hydrocarbon radical having the number of carbon atoms indicated in the prefix. For example, $(C_1-C_6)$alkyl is meant to include methyl, ethyl, n-propyl, 2-propyl, tert-butyl, pentyl, and the like. For each of the definitions herein (e.g., alkyl, alkenyl, alkynyl, alkylene, alkoxy, aralkyloxy etc.), when a prefix is not included to indicate the number of carbon atoms in an alkyl portion, the radical or portion thereof will have six or fewer main chain carbon atoms. In all terms where a prefix indicating the number of carbon atoms is used, the prefix applies to the alkyl portion immediately following the prefix. For example the term heteroaryl$(C_1-C_4)$heteroalkyl indicates from one to four carbon atoms in the heteroalkyl portion.

"Perfluoroalkyl" refers to an alkyl group having the indicated number of carbon atoms, in which some of the attached hydrogen atoms have been replaced with fluorine atoms, in a number ranging from 1 to the maximal number of hydrogen atoms on the alkyl group.

"Alkylene" means a linear saturated divalent hydrocarbon radical or a branched saturated divalent hydrocarbon radical having the number of carbon atoms indicated in the prefix and if unspecified up to six carbon atoms. For example, $(C_1-C_6)$alkylene is meant to include methylene, ethylene, propylene, 2-methylpropylene, pentylene, and the like.

"Alkenyl" means a linear monovalent hydrocarbon radical or a branched monovalent hydrocarbon radical having the number of carbon atoms indicated in the prefix and containing at least one double bond. For example, $(C_2-C_6)$ alkenyl is meant to include ethenyl, propenyl, and the like.

"Alkynyl" means a linear monovalent hydrocarbon radical or a branched monovalent hydrocarbon radical containing at least one triple bond and having the number of carbon atoms indicated in the prefix. For example, $(C_2-C_6)$alkynyl is meant to include ethynyl, propynyl, and the like.

"Alkoxy", "aryloxy", "aralkyloxy", or "heteroaralkyloxy" means a radical —OR where R is an alkyl, aryl, arylalkyl, or heteroarylalkyl respectively, as defined herein, e.g., methoxy, phenoxy, benzyloxy, pyridin-2-ylmethyloxy, and the like.

"Alkoxycarbonylalkyl" means a radical —$R^aC(O)R^b$ where $R^a$ is an alkylene group as defined above and $R^b$ is an alkoxy group as defined above e.g., methoxycarbonylethyl, ethoxycarbonylbutyl, and the like.

"Aryl" means a monovalent monocyclic or bicyclic aromatic hydrocarbon radical of 6 to 10 ring atoms which is optionally substituted independently with one to four substituents, preferably one, two, or three substituents selected from alkyl, cycloalkyl, cycloalkyl-alkyl, phenyl, halo, nitro, cyano, cyanoalkyl, hydroxy, alkoxy, amino, acylamino, mono-alkylamino, di-alkylamino, haloalkyl, haloalkoxy, heteroalkyl, COR (where R is hydrogen, alkyl, cycloalkyl, cycloalkyl-alkyl, phenyl or phenylalkyl), —$S(O)_n$—$R^d$ (where n is an integer from 0 to 2, and where when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino), —NS(O)$_2$R$^f$ (where R$^f$ is alkyl or aryl), —NHCOR$^c$ (where R$^c$ is amino, alkylamino, dialkylamino or (C$_1$-C$_4$)alkoxy), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), —(CR'R")$_n$S(O)$_n$—R$^d$ (where n is an integer from 0 to 2, and where when n is 0, R$^d$ is hydrogen, alkyl, cycloalkyl, or cycloalkylalkyl, and when n is 1 or 2, R$^d$ is alkyl, cycloalkyl, cycloalkylalkyl, amino, acylamino, monoalkylamino, or dialkylamino), —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl (C$_1$-C$_4$) alkoxy or phenylalkyl), or any 2 adjacent carbon atoms are substituted by —O(CH$_2$)$_n$O— (where n is 1 or 2). More specifically the term aryl includes, but is not limited to, phenyl, biphenyl, 1-naphthyl, and 2-naphthyl, cyanophenyl, and the derivatives thereof.

"Arylalkyl" means a radical —R$^a$R$^b$ where R$^a$ is an alkylene group (having six or fewer main chain carbon atoms) and R$^b$ is an aryl group as defined herein, e.g., benzyl, phenylethyl, 3-(3-Chlorophenyl)-2-methylpentyl, and the like with the notation aryl(C$_1$-C$_4$)alkyl indicating from one to four carbon atoms in the alkylene chain.

"Arylheteroalkyl" means a radical —R$^a$R$^b$ where R$^a$ is an heteroalkylene group and R$^b$ is an aryl group as defined herein, e.g., 2-hydroxy-2-phenyl-ethyl, 2-hydroxy-1-hydroxymethyl-2-phenyl-ethyl, and the like.

"Cycloalkyl" means a saturated monovalent cyclic hydrocarbon radical having the number of ring carbon atoms indicated in the prefix and if unspecified from three to seven ring carbon atoms. For example, (C$_3$-C$_7$) cycloalkyl includes cyclopropyl through cycloheptyl. The cycloalkyl may be optionally substituted independently with one, two, or three substituents selected from alkyl, optionally substituted phenyl, or —C(O)R (where R is hydrogen, alkyl, haloalkyl, amino, acylamino, mono-alkylamino, di-alkylamino, hydroxy, alkoxy, or optionally substituted phenyl). More specifically, the term cycloalkyl includes, for example, cyclopropyl, cyclohexyl, phenylcyclohexyl, 4-carboxycyclohexyl, 2-Carboxamidocyclohexyl, 2-dimethylaminocarbonyl-cyclohexyl, and the like.

"Cycloalkyl-alkyl" means a radical —R$^a$R$^b$ where R$^a$ is an alkylene group and R$^b$ is a cycloalkyl group as defined herein, e.g., cyclopropylmethyl, cyclohexylpropyl, 3-cyclohexyl-2-methylpropyl, and the like. The prefix indicating the number of carbon atoms (e.g., C$_3$-C$_7$) refers to the number of ring carbon atoms in the cycloalkyl portion.

"Haloalkyl" means alkyl substituted with one or more same or different halo atoms, e.g., —CH$_2$Cl, —CF$_3$, —CH$_2$CF$_3$, —CH$_2$CCl$_3$, and the like, and further includes those alkyl groups such as perfluoroalkyl in which all hydrogen atoms are replaced by fluorine atoms. The prefix "halo" and the term "halogen" when used to describe a substituent, refer to —F, —Cl, —Br and —I.

"Heteroalkyl" means an alkyl radical as defined herein with one, two or three substituents independently selected from cyano, —OR$^a$, —NR$^b$R$^c$, and S(O)$_n$R$^d$ (where n is an integer from 0 to 2 ); with the understanding that the point of attachment of the heteroalkyl radical is through a carbon atom of the heteroalkyl radical. R$^a$ is hydrogen, alkyl, cycloalkyl, cycloalkyl-alkyl, aryl, aralkyl, alkoxycarbonyl, aryloxycarbonyl, carboxamido, or mono- or di-alkylcarbamoyl. R$^b$ is hydrogen, alkyl, cycloalkyl, cycloalkyl-alkyl, aryl or aralkyl. R$^c$ is hydrogen, alkyl, cycloalkyl, cycloalkyl-alkyl, aryl, aralkyl, alkoxycarbonyl, aryloxycarbonyl, carboxamido, mono- or di-alkylcarbamoyl, alkylsulfonyl, —C(O)R', or —S(O)$_n$R' (where n is an integer from 0 to 2; where R' is hydrogen, alkyl or aryl). R$^d$ is hydrogen (provided that n is 0), alkyl, cycloalkyl, cycloalkyl-alkyl, aryl, aralkyl, amino, monoalkylamino, di-alkylamino, or hydroxyalkyl. Representative examples include, 2-hydroxyethyl, 2,3-dihydroxypropyl, 2-methoxyethyl,benzyloxymethyl, 2-cyanoethyl, and 2-methylsulfonyl-ethyl. Additionally, the prefix indicating the number of carbon atoms (e.g., C$_1$–C$_{10}$) refers to the total number of carbon atoms in the portion of the heteroalkyl group exclusive of the cyano, —OR$^a$, —NR$^b$R$^c$, or —S(O)$_n$R$^d$ portions.

"Heteroaryl" means a monovalent monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently with one to four substituents, preferably one or two substituents, selected from alkyl, cycloalkyl, cycloalkyl-alkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl, —(CR'R")$_n$—COOR (where n is an integer from 0 to 5, R' and R" are independently hydrogen or alkyl, and R is hydrogen, alkyl, cycloalkyl, cycloalkyl-alkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkyl-alkyl, phenyl or phenylalkyl). More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyridazinyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, and the derivatives thereof.

"Heteroarylalkyl" means a radical —R$^a$R$^b$ where R$^a$ is an alkylene group and R$^b$ is a heteroaryl group as defined herein, e.g., pyridin-3-ylmethyl, 3-(benzofuran-2-yl)propyl, and the like.

"Heterocyclyl" means a saturated or unsaturated non-aromatic cyclic radical of 3 to 8 ring atoms in which one or two ring atoms are heteroatoms selected from O, NR (where R is independently hydrogen, alkyl, or any of the substituents listed below), or S(O)$_n$ (where n is an integer from 0 to 2), the remaining ring atoms being C, where one or two C atoms may optionally be replaced by a carbonyl group. The heterocyclyl ring may be optionally substituted independently with one, two, or three substituents selected from alkyl, cycloalkyl, cycloalkyl-alkyl, arylalkyl, halo, nitro, cyano, cyanoalkyl, hydroxy, alkoxy, amino, mono-alkylamino, di-alkylamino, haloalkyl, haloalkoxy, —(CR'R")$_n$—COR (where n is an integer from 0 to 5, R' and R" are independently hydrogen or alkyl, R is hydrogen, alkyl, cycloalkyl, cycloalkyl-alkyl, phenyl, or phenylalkyl), —(CR'R")$_n$—COOR (n is an integer from 0 to 5, R' and R" are independently hydrogen or alkyl, and R is hydrogen, alkyl, cycloalkyl, cycloalkyl-alkyl, phenyl or phenylalkyl), —(CR'R")$_n$—C(=Q)NR$^a$R$^b$ (where Q is O or S, n is an integer from 0 to 5, R' and R" are independently hydrogen or alkyl, and R$^a$ and R$^b$ are, independently of each other, hydrogen, alkyl, cycloalkyl, cycloalkylalkyl, heteroalkyl, phenyl or phenylalkyl), or —(CR'R")$_{n1}$—S(O)$_n$R$^d$ (where n1 is an integer from 0 to 5, R$^d$ is hydrogen (provided that n is 0), alkyl, cycloalkyl, cycloalkyl-alkyl, aryl, aralkyl, amino, mono-alkylamino, di-alkylamino, or hydroxyalkyl, and n is an integer from 0 to 2). More specifically the term heterocyclyl includes, but is not limited to, tetrahydropyranyl, piperidino, N-methylpiperidin-3-yl, piperazino, 4-methanesulfonyl-1-piperazino, 4-dimethylaminosulfonyl-1-piperazino, N-methylpyrrolidin-3-yl, 3-pyrrolidino, 2-pyrrolidon-1-yl, morpholino, thiomorpholino, thiomorpholino-1-oxide, thiomorpholino-1,1-dioxide, pyrrolidinyl, and the derivatives thereof.

"Heterocyclylalkyl" means a radical —R$^a$R$^b$ where R$^a$ is an alkylene group and R$^b$ is a heterocyclyl group as defined herein, e.g., tetrahydropyran-2-ylmethyl, 4-methylpiperazin-1-ylethyl, 3-piperidinylmethyl, and the like.

"Heterosubstituted cycloalkyl" means a cycloalkyl group wherein one, two, or three hydrogen atoms are replaced by substituents independently selected from the group consisting of cyano, cyanomethyl, hydroxy, hydroxymethyl, alkoxy, amino, acylamino, mono-alkylamino, di-alkylamino, —SO$_n$R (where n is an integer from 0 to 2 and when n is 0, R is hydrogen or alkyl and when n is 1 or 2, R is alkyl, cycloalkyl, cycloalkylalkyl, aryl, aralkyl, heteroaryl, amino, acylamino, mono-alkylamino, di-alkylamino, or hydroxyalkyl), or —NHSO$_2$R where R is alkyl or aryl. Examples include 4-hydroxycyclohexyl, 2-aminocyclohexyl etc.

"Hydroxyalkyl" means an alkyl radical as defined herein, substituted with one or more, preferably one, two or three hydroxy groups, provided that the same carbon atom does not carry more than one hydroxy group. Representative examples include, but are not limited to, 2-hydroxyethyl, 2-hydroxypropyl, 3-hydroxypropyl, 1-hydroxymethyl-2-methylpropyl, 2-hydroxybutyl, 3-hydroxybutyl, 4-hydroxybutyl, 2,3-dihydroxypropyl, 1-hydroxymethyl-2-hydroxyethyl, 2,3-dihydroxybutyl, 3,4-dihydroxybutyl and 2-hydroxymethyl-3-hydroxypropyl, preferably 2-hydroxyethyl, 2,3-dihydroxypropyl and 1-hydroxymethyl-2-hydroxyethyl. Accordingly, as used herein, the term "hydroxyalkyl" is used to define a subset of heteroalkyl groups.

"Optionally substituted phenyl" means a phenyl ring which is optionally substituted independently with one to four substituents, preferably one or two substituents selected from alkyl, cycloalkyl, cycloalkyl-alkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl, —NHS(O)$_2$R$^f$ (where R$^f$ is alkyl or aryl), —NHCOR$^c$ (where R$^c$ is amino, alkylamino, dialkylamino or (C$_1$–C$_4$)alkoxy), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl, (C$_1$–C$_4$)alkoxy or phenylalkyl) or or any 2 adjacent carbon atoms are substituted by —O(CH$_2$)$_n$O— (where n is 1 or 2).

"Leaving group" has the meaning conventionally associated with it in synthetic organic chemistry i.e., an atom or group capable of being displaced by a nucleophile and includes halo (such as chloro, bromo, iodo), alkanesulfonyloxy, arenesulfonyloxy, alkylcarbonyloxy (e.g. acetoxy), arylcarbonyloxy, mesyloxy, tosyloxy, trifluoromethanesulfonyloxy, aryloxy (e.g., 2,4-dinitrophenoxy), methoxy, N, O-dimethylhydroxylamino, and the like.

"Pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-Chlorobenzenesulfonic acid, 2-napthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynapthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Pro-drugs" means any compound which releases an active parent drug according to Formula (I) in vivo when such prodrug is administered to a mammalian subject. Prodrugs of a compound of Formula (I) are prepared by modifying functional groups present in the compound of Formula (I) in such a way that the modifications may be cleaved in vivo to release the parent compound. Prodrugs include compounds of Formula (I) wherein a hydroxy, amino, or sulfhydryl group in a compound of Formula (I) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of Formula (I), and the like.

"Protecting group" refers to a grouping of atoms that when attached to a reactive group in a molecule masks, reduces or prevents that reactivity. Examples of protecting groups can be found in T. W. Greene and P. G. Futs, Protective Groups in Organic Chemistry, (Wiley, 2nd ed. 1999) and Harrison and Harrison et al., Compendium of Synthetic Organic Methods, Vols. 1–8 (John Wiley and Sons. 1971–1996). Representative amino protecting groups include formyl, acetyl, trifluoroacetyl, benzyl, benzyloxy-carbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC) and the like. Representative hydroxy protecting groups include those where the hydroxy group is either acylated or alkylated such as benzyl and trityl ethers as well as alkyl ethers, tetrahydropyranyl ethers, trialkylsilyl ethers and allyl ethers.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Optional" or "optionally" in the above definitions means that the subsequently described event or circumstance may but need not occur, and that the description includes instances where the event or circumstance occurs and instances in which it does not. For example, "heterocyclo group optionally mono- or di-substituted with an alkyl group" means that the alkyl may but need not be present, and the description includes situations where the heterocyclo group is mono- or disubstituted with an alkyl group and situations where the heterocyclo group is not substituted with the alkyl group.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see discussion in Chapter 4 of "Advanced Organic Chemistry", 4th edition J. March, John Wiley and Sons, New York, 1992).

The compounds of the present invention can also be produced in radiolabeled form and are useful in assays for evaluating the binding capabilities of compounds that interact with IKKα and with IKKβ.

Embodiments of the Invention

Compounds

In one aspect, the present invention provides compounds useful in the treatment of inflammatory, metabolic or malignant conditions, having the formula:

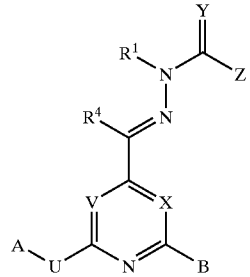

(I)

In Formula (I), one of either V or X is N and the other is $-CR_a$, or both V and X are $-CR_a$ (where each $R_a$ is independently hydrogen, alkyl, cycloalkyl or cycloalkylalkyl). Preferably, V is N and X is CH.

Y represents O, S or N(R), wherein R is H, CN, $NO_2$, $(C_1-C_{10})$alkyl, $(C_3-C_7)$cycloalkyl, $(C_3-C_7)$cycloalkyl-alkyl, $(C_3-C_{10})$alkenyl or $(C_2-C_{10})$alkynyl. Preferably, Y is O or S. More preferably Y is S.

Z represents H, $(C_1-C_6)$alkyl, $(C_3-C_7)$cycloalkyl, $(C_3-C_7)$cycloalkyl-alkyl, $(C_2-C_6)$alkenyl, $(C_2-C_6)$alkynyl, aryl or $N(R^2)(R^3)$ where $R^2$ and $R^3$ are each independently H, $(C_1-C_{10})$alkyl, $(C_3-C_{10})$alkenyl, $(C_2-C_{10})$alkynyl, $(C_3-C_7)$cycloalkyl, $(C_3-C_7)$ cycloalkyl-alkyl, or $(C_1-C_{10})$ heteroalkyl, or $R^2$ and $R^3$ can be combined to form a 5–7-membered heterocyclyl ring.

Preferably, Z is $(C_1-C_6)$alkyl or $N(R^2)(R^3)$. More preferably Z is NHMe or $NH_2$, most preferably Z is $NH_2$.

$R^1$ represents H, $(C_1-C_{10})$alkyl, $(C_3-C_{10})$alkenyl, $(C_2-C_{10})$alkynyl, $(C_3-C_7)$cycloalkyl, $(C_3-C_7)$cycloalkyl-alkyl, $(C_1-C_{10})$heteroalkyl, heterocyclyl, heterocyclylalkyl, aryl, aryl$(C_1-C_4)$alkyl, aryl$(C_1-C_4)$heteroalkyl, heteroaryl $(C_1-C_4)$alkyl, heteroaryl$(C_1-C_4)$heteroalkyl, or alkylene-C$(O)R^{11}$.

$R^{11}$ is hydrogen, $(C_1-C_6)$alkyl or $NR^{12}R^{13}$ (where $R^{12}$ and $R^{13}$ are independently hydrogen, $(C_1-C_6)$alkyl or heteroalkyl);

Preferably, $R^1$ is $(C_1-C_{10})$alkyl, $(C_1-C_{10})$heteroalkyl, heterocyclylalkyl, heteroaryl$(C_1-C_4)$alkyl or alkylene-C(O) $R^{11}$. More preferably, $R^1$ is $(C_1-C_{10})$alkyl, $(C_1-C_{10})$ heteroalkyl or heterocyclylalkyl.

$R^4$ represents H, alkyl, $(C_3-C_7)$cycloalkyl, $(C_3-C_7)$ cycloalkyl-alkyl, $(C_2-C_6)$alkenyl or $(C_2-C_6)$alkynyl. Preferably $R^4$ is H or alkyl. Most preferably, $R^4$ is H.

A represents H, $(C_1-C_{10})$alkyl, $(C_3-C_{10})$alkenyl, $(C_2-C_{10})$alkynyl, $(C_3-C_7)$cycloalkyl, $(C_3-C_7)$cycloalkyl-alkyl, $(C_1-C_{10})$heteroalkyl, heterocyclyl, heterocyclylalkyl, heterosubstituted cycloalkyl, aryl, aryl$(C_1-C_4)$alkyl, aryl $(C_1-C_4)$heteroalkyl, heteroaryl, heteroaryl$(C_1-C_4)$alkyl, heteroaryl$(C_1-C_4)$heteroalkyl or $R^aNHC(=X)-$ wherein $R^a$ is $(C_1-C_4)$alkyl or aryl and X is O or S.

Preferably, A is $(C_1-C_{10})$alkyl, $(C_3-C_7)$cycloalkyl, $(C_1-C_{10})$heteroalkyl, heterocyclyl, heterocyclylalkyl, heterosubstituted cycloalkyl, aryl, aryl$(C_1-C_4)$alkyl, or heteroaryl. More preferably, A represents $(C_3-C_7)$cycloalkyl, $(C_1-C_{10})$heteroalkyl, heterocyclyl, heterosubstituted cycloalkyl, aryl, aryl$(C_1-C_4)$alkyl or heteroaryl.

B represents a substituted or unsubstituted five- or six-membered aromatic ring containing at least one nitrogen atom, and from 0 to 3 additional heteroatoms, wherein the B ring substituents are selected from halogen, $CF_3$, $CF_3O$, $(C_1-C_6)$alkyl, amino, $(C_1-C_6)$alkylamino, di$(C_1-C_6)$ alkylamino, cyano, nitro, sulfonamido, acyl, acylamino, and carboxamido. Preferably, the substituents on B are halo, $CF_3$, $CH_3$ or amino, more preferably $CH_3$.

Preferably, B contains a nitrogen atom at a position two atoms away from the atom attaching B to the remainder of the molecule. More preferably, B is selected from substituted or unsubstituted imidazolyl, substituted or unsubstituted thiazolyl and substituted or unsubstituted triazolyl. Still more preferably, B is selected from 1-methylimidazol-5-yl, 1-(trifluoromethyl)imidazol-5-yl, 5-methylimidazol-1-yl, 5-(trifluoromethyl)imidazol-1-yl, thiazol-5-yl, imidazol-1-yl and 4-methyl-1,2,4-triazol-3-yl.

The letter U represents $NR^5$, O or S, wherein $R^5$ is H or $(C_1-C_6)$alkyl. Preferably, U represents $NR^5$. More preferably, $R^5$ is H, i.e. U is NH.

In another group of embodiments, V is CH and X is N. Within this group of embodiments, Y is preferably O or S, more preferably S. Preferably, Z is $(C_1-C_6)$alkyl or $N(R^2)(R^3)$. More preferably Z is NHMe or $NH_2$, most preferably Z is $NH_2$. Preferably, $R^4$ is H or $CH_3$, more preferably H. Preferably, A is either selected from $(C_1-C_{10})$alkyl, $(C_1-C_{10})$heteroalkyl, aryl$(C_1-C_4)$alkyl, $(C_3-C_7)$cycloalkyl and aryl. Also, preferred in this group of embodiments are those in which B contains a nitrogen atom at a position two atoms away from the atom attaching B to the remainder of the molecule. More preferably, B is selected from substituted or unsubstituted imidazolyl, substituted or unsubstituted thiazolyl and substituted or unsubstituted triazolyl. Also, preferred in this group of embodiments are those in which U is $NR^5$, more preferably NH.

In another group of embodiments, V is CH and X is CH. In yet another group of preferred embodiments, Y is S; Z is $NH_2$; and $R^1$ is $CH_3$. In this group of embodiments, preferred groups for each of A and B are the same as have been described above.

A number of different substituent preferences have been given above and following any of these substituent preferences results in a compound of the invention that is more preferred than one in which the particular substituent preference is not followed. However, these substituent preferences are generally independent, although some preferences are mutually exclusive, and following more than one of these preferences may result in a more preferred compound than one in which fewer of the substituent preferences are followed.

Particularly preferred compounds of the present invention are selected from those provided in the Examples that follow.

The present invention further provides methods of preparing anti-inflammation agents, comprising contacting a precursor compound having the formula:

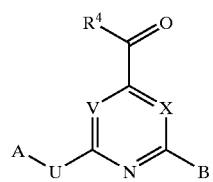

wherein A, U, V, X, B and $R^4$ are as defined in the Summary of the Invention. with a compound having the formula:

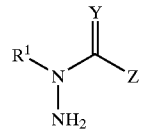

wherein Y is selected from the group consisting of O and S and Z and R1 are as defined in the Summary of the Invention under conditions sufficient to produce compounds having the formula:

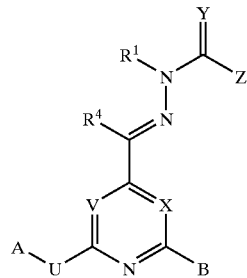

wherein each of A, B, $R^1$, $R^4$, U, V, X, Y and Z have the meanings provided above.

Exemplary conditions are provided in the examples below, with the understanding that the skilled practitioner can adjust solvents, temperature, time of reaction, workup conditions and the like to produce the desired compounds.

In view of the methods provided herein, one of skill will also appreciate that certain compounds are particularly useful in the preparation of the subject antiinflammation agents. Accordingly, the present invention provides in another aspect compounds of the formula:

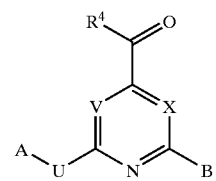

wherein V, X, A, U, B and $R^4$ are as defined in the Summary of the Invention.

Compositions

In addition to the compounds provided above, the present invention further provides pharmaceutical compositions comprising one or more of the subject compounds in admixture with a pharmaceutically acceptable excipient.

In one embodiment, the invention provides the subject compounds combined with a pharmaceutically acceptable excipient such as sterile saline or other medium, water, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include solid, semi-solid or liquid media including water and non-toxic organic solvents.

In another embodiment, the invention provides the subject compounds in the form of a pro-drug, which can be metabolically or chemically converted to the subject compound by the recipient host. A wide variety of pro-drug derivatives are known in the art such as those that rely on hydrolytic cleavage or oxidative activation of the prodrug.

The compositions may be provided in any convenient form, including tablets, capsules, lozenges, troches, hard candies, powders, sprays, creams, suppositories, etc. As such, the compositions, in pharmaceutically acceptable dosage units or in bulk, may be incorporated into a wide variety of containers. For example, dosage units may be included in a variety of containers including capsules, pills, etc.

Still other compositions of the present invention are those that combine two or more of the present compounds in one formulation, or one compound from the present invention with a second anti-inflammatory, antiproliferative or antidiabetic agent.

Methods of Use

In yet another aspect, the present invention provides methods of treating IKK-mediated conditions or diseases by administering to a subject having such a disease or condition, a therapeutically effective amount of a compound of Formula (I) above. The "subject" is defined herein to include animals such as mammals, including, but not limited to, primates (e.g., humans), cows, sheep, goats, horses, dogs, cats, rabbits, rats, mice and the like.

The term "therapeutically effective amount" means the amount of the subject compound that will elicit the biological or medical response of a tissue, system, animal or human that is being sought by the researcher, veterinarian, medical doctor or other clinician.

Diseases and conditions associated with inflammation, infection and cancer can be treated with the present compounds and compositions. In one group of embodiments, diseases or conditions, including chronic diseases, of humans or other species can be treated with inhibitors of IKK function. These diseases or conditions include: (1) inflammatory or allergic diseases such as systemic anaphylaxis or hypersensitivity responses, drug allergies, insect sting allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis; spondyloarthropathies; scleroderma; respiratory allergic diseases such as asthma, allergic rhinitis, hypersensitivity lung diseases, and the like, (2) autoimmune diseases, such as arthritis (rheumatoid and psoriatic), osteoarthritis, multiple sclerosis, systemic lupus erythematosus, diabetes mellitus, glomerulonephritis, and the like, (3) graft rejection (including allograft rejection and graft-v-host disease), and (4) other diseases in which undesired inflammatory responses are to be inhibited (e.g., atherosclerosis, myositis, neurological conditions such as stroke and closed-head injuries, neurodegenerative diseases, Alzheimer's disease, encephalitis, meningitis, osteoporosis, gout, *hepatitis*, nephritis, sepsis, sarcoidosis, conjunctivitis, otitis, chronic obstructive pulmonary disease, sinusitis and Behcet's syndrome); (5) in another group of embodiments, diseases or conditions are treated with inhibitors of IKK function that will promote cell death; examples of these diseases include, but are not limited to, neoplastic diseases such as solid tumors (e.g. non-Hodgins lymphoma), skin cancer, melanoma, lymphoma, and diseases in which angiogenesis and neovascularization play a role; (6) other metabolic disorders that are sensitive to inhibition of TNF or IL-1 signaling, such as obesity for example.

Depending on the disease to be treated and the subject's condition, the compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

In the treatment or prevention of conditions which require NF-κB m modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the present invention can be combined with other compounds having related utilities to prevent and treat inflammatory and immunoregulatory disorders and diseases, including asthma and allergic diseases, as well as autoimmune pathologies such as rheumatoid arthritis and atherosclerosis, and those pathologies noted above.

For example, in the treatment or prevention of inflammation, the present compounds may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin receptor antagonist, such as an interleukin-1 receptor antagonist, an NMDA receptor antagonist, an inhibitor of nitric oxide or an inhibitor of the synthesis of nitric oxide, a non-steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sulindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antitussive such as codeine, hydrocodone, caramiphen, carbetapentane, or dextramethorphan; a diuretic; and a sedating or non-sedating antihistamine. Each of the above agents may be administered, by a route and in an amount commonly used therefor, contemporaneously or sequentially with a compound of the present invention. When a compound of the present invention is used contemporaneously with one or more other drugs, in some cases a pharmaceutical composition containing such other drugs in addition to the compound of the present invention may be preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists; (b) steroids such as beclomethasone, methylprednisolone, betamethasone, prednisone, dexamethasone, and hydrocortisone; (c) immunosuppressants such as methotrexate cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as beta-adrenergic agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal anti-inflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) anti-diabetic agents such as insulin, sulfonylureas, biguanides (metformin), α-glucosidase inhibitors (acarbose) and glitazones (troglitazone, rosiglitazone and pioglitazone); (j) preparations of interferon beta (interferon beta-1.alpha, interferon beta-1.beta.); (k) other compounds such as 5-aminosalicylic acid and prodrugs thereof, antimetabolites such as methotrexate, azathioprine and 6-mercaptopurine, and cytotoxic cancer chemotherapeutic agents; and (1) agents that directly or indirectly interfere with cytokine signalling, such as soluble TNF receptors, TNF antibodies, soluble IL-1 receptors, IL-1 antibodies, and the like. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

EXAMPLES

Reagents and solvents used below can be obtained from commercial sources such as Aldrich Chemical Co. (Milwaukee, Wis., USA). $^1$H-NMR spectra were recorded on a Bruker DPX 300 NMR spectrometer. Significant peaks are tabulated in the order: number of protons, multiplicity (s, singlet; d, doublet; t, triplet; q, quartet; m, multiplet; br s, broad singlet) and coupling constant(s) in Hertz. Electrospray ionization (ESI) mass spectrometry analysis was conducted on a Micromass Platform LC electrospray mass spectrometer using the Shimadzu LC-8A HPLC for sample delivery. Normally the analyte was dissolved in DMSO and 20 microliter was infused with the delivery solvent into the mass spectrometer, which scanned from 100 to 800 daltons. All compounds could be analyzed in the positive ESI mode, using acetonitrile/water with 0.1% trifluoroacetic acid as the delivery solvent.

General Scheme for Synthesis

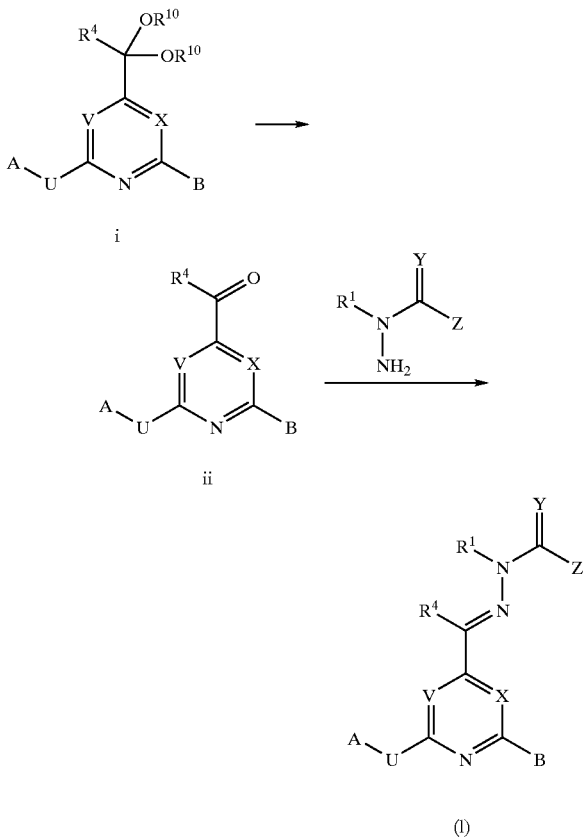

The synthesis of the target compounds is generally accomplished as shown in Scheme 1 by reaction of the appropriate aldehyde (or ketone when $R^4$ is other than H) ii with the appropriately substituted hydrazine derivative. In some cases, the aldehyde (or ketone) intermediate ii is not fully isolated or characterized, but is simply synthesized from the corresponding acetal (or ketal) and used directly in the final reaction. The final products can be isolated and purified, if necessary, by filtration, recrystallization and/or chromatography, as appropriate.

The starting acetals (or ketals) can be prepared by a variety of methods generally known to those skilled in the art of organic synthesis. Representative methods for the synthesis of these compounds are provided in the Examples below.

Preparation of Synthetic Intermediates

For compounds of the invention in which V=N, X=CH and $R^4$ is H, one can synthesize the intermediate acetal using the following general synthetic Scheme 2:

Scheme 2

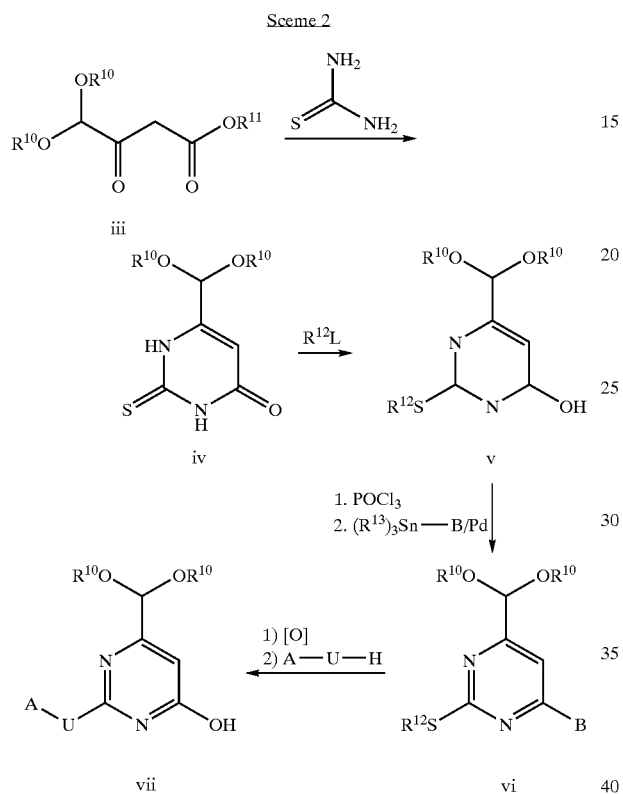

Keto ester iii is reacted with thiourea to provide pyrimidinol iv. Compound iv is alkylated at the pendant thio group affording pyrimidinol v. Conversion of the hydroxyl group of v to a chloride followed by a palladium cross coupling reaction using a tin derivative yields vi. Oxidation of the sulfanyl group followed by nucleophilic displacement produces the target compound vii. (For sake of exemplification, $R^{10}$, $R^{11}$ and $R^{13}$ are alkyl and $R^{12}$ is aralkyl.)

Alternatively, one can synthesize acetal vii following general synthetic Scheme 3:

Scheme 3

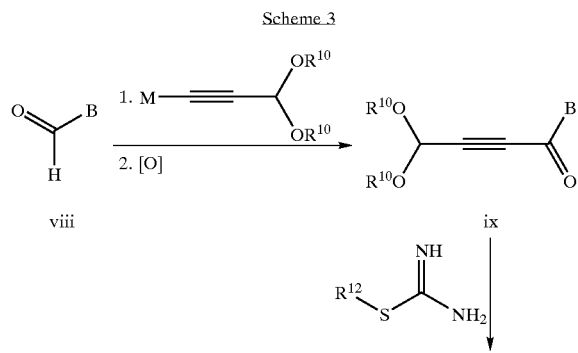

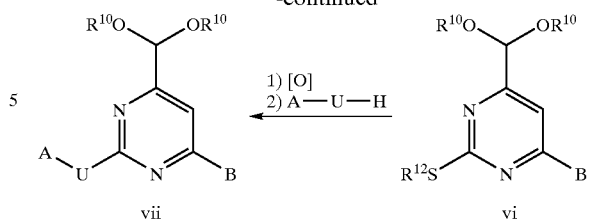

Aldehyde viii is reacted with a propargyl anion (M is a metal) and subsequently oxidized to provide ketone ix. The combination of ketone ix with a thiopseudourea affords pyrimidine vi, which is converted to vii as above.

Example 1

Synthesis of 2-isopropylamino-6-(1-methyl-1-H-imidazol-5-yl)-pyrimidine-4-carbaldehyde 2-methyl-thiosemicarbazone

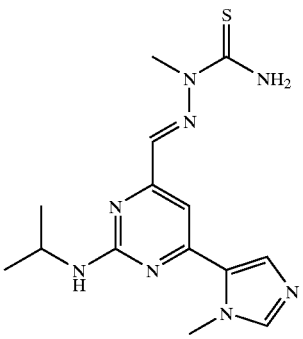

Step 1

Ethyl diethoxyacetate (10.4 mL, 60.0 mmol) and EtOAc (9.0 mL, 90 mmol) were heated at 85° C. and then treated with sodium metal (1.44 g, 60 mmol) in small pieces. After 2 h of heating, an additional portion of EtOAc was added (9.0 mL, 90 mmol) followed by an additional portion of sodium metal (1.44 g, 60 mmol), and heating was maintained for an additional 3 h. The reaction was then cooled to room temperature and stirred overnight. The reaction was then poured onto water, acidified with 1 N HCl, and extracted with diethyl ether (3x). The organics were washed with saturated $NaHCO_3$ (3x) and saturated NaCl, dried over $MgSO_4$, and concentrated in vacuo. The crude product was dried under vacuum (0.5 mm Hg) while being heated in an oil bath at 80° C. to remove any ethyl acetoacetate that may have been produced. To a solution of the crude keto ester and thiourea (4.57 g, 60 mmol) in EtOH (45 mL), was added 25% NaOMe (13 mL, 57 mmol, Aldrich) and heated at reflux for 4 h. The reaction was cooled for 10 minutes, diluted with water (50 mL), treated with benzyl bromide (9.4 g, 55 mmol), and then stirred warm. Crystals formed after 5 minutes, and the reaction was allowed to cool to room temperature and sit undisturbed for 1 h. The white solid was diluted with water and filtered to give 2-benzylsulfanyl-6-diethoxymethyl-pyrimidin-4-ol (9.5 g, 29.6 mmol, 50%).

Step 2

The hydroxy pyrimidine (10.0 g, 31 mmol) was stirred with 2-picoline (2.0 mL). To this was added phosphorus oxychloride (20 mL) while cooling the reaction to 0° C. The reaction was stirred for 2 h, allowing it to warm to room temperature, and then poured over ice. The aqueous mixture was extraced with diethyl ether (3x), the ether extracts were combined and washed with water, saturated NaHCO₃, brine, and dried over MgSO₄. The ether was removed in vacuo, and the crude product immediately placed in a mixture of 50 ml of absolute ethanol and 50 ml triethyl orthoformate, followed by the addition of p-toluenesulfonic acid (100 mg). The reaction was heated at reflux for 1.5 h, cooled to room temperature, and diluted with diethyl ether. The mixture was washed with water, saturated NaHCO₃, brine, and dried over MgSO₄. The solvent was removed in vacuo and the residue chromatographed over silica gel (EtOAc/hexanes 5:95) to give the chloride as an oil (7.9 g, 23 mmol, 74%).

Step 3

A solution of the chloro pyrimidine (2.6 g, 7.7 mmol) and 1-methyl-5-tributyltin-imidazole (3.0 g, 8.1 mmol), in benzene (20 mL) was deoxygenated by bubbling N₂ gas through for 2 minutes at which point tetrakis(triphenylphosphine) palladium (0) was added (445 mg, 0.38 mmol) and the reaction was heated to reflux under N₂ for 3.5 h. The reaction was cooled, placed on the top of a silica gel column and eluted with MeOH/CH₂Cl₂ 5:95 to give the pyrimidine imidazole as an oil (3.5 g), which contained some tributyl tin impurities.

Step 4

To a solution of the sulfide (3.5 g from the previous step) in a mixture of 50 mL EtOH and 50 mL water was added oxone (16 g). The reaction was stirred for 12 h, diluted with saturated NaHCO₃, extracted with EtOAc (3×), washed with water and brine, and dried over MgSO₄. After removal of solvents in vacuo, the residue was chromatographed on silica gel EtOAc/hexanes 1:1 followed by MeOH/CH₂Cl₂ 5:95) to give the corresponding sulfone (1.01 g, 2.42 mmol, 31% for two steps).

Step 5

A solution of the sulfone (200 mg, 0.52 mmol) and isopropyl amine (1.0 mL) was stirred in THF (2.0 mL) at room temperature for 14 h. The mixture was placed on top of a silica gel column and purified (EtOAc/hexanes 1:1 followed by MeOH/CH₂Cl₂ 5:95) to give the desired amino pyrimidine acetal (110 mg, 0.345 mmol, 66%).

Step 6

The acetal (410 mg, 1.28 mmol) was heated in a mixture of 1N HCl (3 mL) and THF (3 mL) for 1 h. The reaction was cooled and diluted with EtOAc and water. Solid Na₂CO₃ was added until the aqueous phase was basic, extracted with EtOAc (2×), the organic phase washed with brine and dried over MgSO₄. The solvents were removed in vacuo to give the aldehyde (200 mg, 0.816 mmol, 64%) as a solid, Step 7

A solution of the aldehyde (50 mg, 0.204 mmol) and 2-methyl-3-thiosemicarbazide (35 mg, 0.33 mmol, Aldrich) in EtOH (2 mL) was heated to 60° C. The reaction stirred for 14 h and then cooled to room temperature. The precipitate was removed by filtration, washed with water (3×), and then with diethyl ether (3×) to give 2-isopropylamino-6-(1-methyl-1-H-imidazol-5-yl)-pyrimidine-4-carbaldehyde 2-methyl-thiosemicarbazone (48 mg, 0.145 mmol, 71%). MS (ES+): 333.

2-n-butyl-6-(1-methyl-1-H-imidazol-5-yl)-pyrimidine-4-carbaldehyde 2-methyl-thiosemicarbazone was prepared as described in Example 1, but 1-butylamine was substituted for isopropylamine in step 5. MS (EI): (M⁺) 346.

Alternative Synthesis of 2-benzylsulfanyl-4-diethoxymethyl-6-(1-methyl-1H-imidazol-5-yl)-pyrimidine

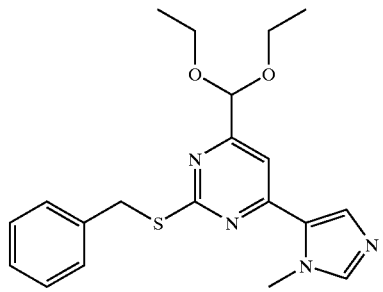

Step 1

To a solution of propiolaldehyde diethylacetal (2.0 g, 16 mmol, Aldrich) in 20 mL of dry THF at −78° C. was added n-butyllithium (6.4 mL, 16 mmol) dropwise. The resulting yellow solution was allowed to warm to −20° C. over 45 min and then recooled in a dry-ice acetone bath. To this was added 2-t-butyldimethylsilyl-1-methylimidazole-5-carboxaldehyde (2.2 g, 10 mmol; prepared according to Walters, et. al. Tetrahedron Lett. 1994, 35, 8307–8310), in 10 mL of dry THF, the reaction mixture was stirred for 15 min and then quenched with saturated ammonium chloride. The reaction mixture was diluted with water and extracted with EtOAc. The EtOAc layer was washed with brine, dried over Na₂SO₄ and the solvent concentrated. The crude product and MnO₂ (10 g) in 100 mL of CH₂Cl₂ was stirred overnight. The reaction mixture was filtered through Celite and washed well with CH₂Cl₂. The solvent was removed on a rotary evaporator and the residue was purified by flash chromatography (silica gel, acetone/hexane 15:85) to obtain the desired ketone as an oil (2.5 g, 71%). ¹H NMR (CDCl₃): δ 8.12 (s, 1H), 5.45 (s, 1H), 4.05 (s, 3H), 3.9–3.61 (m, 6H), 1.25 (s, 3H), 0.96 (s, 9H), 0.43 (s, 6H). MS (EI): (M⁺+1) 351.

Step 2

A mixture of 2-benzyl-2-thiopseudourea hydrochloride (1.04 g, 5.1 mmol, Aldrich), the above ketone (1.5 g, 4.28 mmol) and potassium carbonate (0.7 g, 5 mmol) was suspended in 20 mL of acetonitrile and heated at 80° C. overnight. The resulting mixture was diluted with water and extracted with EtOAc. The organic layer was washed with brine, dried over Na₂SO₄, concentrated, and the residue was purified by flash chromatography (silica gel, MeOH/dichloromethane 3:97) to obtain of 2-benzylsulfanyl-4-diethoxymethyl-6-(1-methyl-1H-imidazol-5-yl)-pyrimidine as an oil (1.3 g, 80%). ¹HNMR (CDCl₃) δ 7.6 (s,1H), 7.4 (s, 1H), 7.35–7.3 (m, 2H), 7.25–7.1 (m, 4H), 5–19 (s, 1H), 4.34 (s, 2H), 3.86 (s, 3H), 3.7–3.5 (m, 4H), 3.15 (t, 6H). MS (EI): (M⁺+1) 385.

Example 2

2-(4-Methoxy-phenylamino)-6-(1-methyl-3H-imidazol-5-yl)-pyrimidine-4-carbaldehyde 2-methyl-thiosemicarbazone

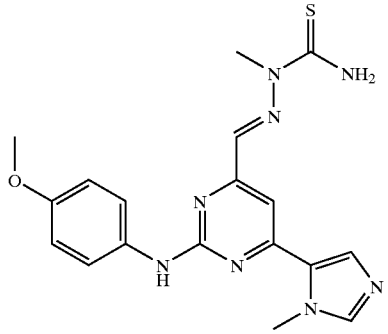

Step 1

To a solution of p-anisidine (600 mg, 4.87 mmol) in dry THF (5 ml) was added N,N'-bis-Boc-1-guanylpyrazole (1.44 g, 4.63 mmol). The resulting mixture was stirred at room temperature for 40 h. After removing volatiles, the crude material was loaded onto a flash column (silica gel, 2% to 7.5% EtOAc/hexanes 2:98 followed by 7.5:92.5) to give the corresponding protected guanidine (1.71 g) as a white solid. MS (ES+): 366.

Step 2

To a solution of the protected guanidine (1.7 g, 4.65 mmol) in dry EtOAc (20 ml) was added tin(IV) chloride (2.2 ml, 4 eq). The mixture was stirred for 1 h and then all volatiles were removed under vacuo. EtOAc (20 ml) was added and the material again stripped under vacuo (repeat one more time). MeOH (10 ml) was added and the material was stirred for 1 minute and then placed under vacuo to remove 90% of the solvent. Ether (15 ml) was added and the product slowly crystallized out. The product was collected by filtration and washed with ether to afford 4-methoxyphenylguanidine hydrochloride (853 mg) as a pink-white solid. MS (ES+): 166.

Step 3

To a mixture of 4-methoxyphenylguanidine hydrochloride (850 mg, 4.21 mmol) and 4,4-diethoxy-3-oxo-butyric acid ethyl ester (2.76 g, 12.65 mmol) in dry ethanol (15 ml) was added $K_2CO_3$ (434 mg, 3.2 mmol). The mixture was heated to reflux overnight. Extra $K_2CO_3$ (1.16 g) was added and heating continued for 1 h. The material was cooled to room temperature and the EtOH was removed under vacuo. The remainder was taken up in EtOAc (80 ml) and partitioned with an equal volume of water. The organic phase was collected and washed with an equal volume of 50% diluted brine. The aqueous phase was back-extracted with EtOAc (2×50 ml), the organic phases combined, dried onver $MgSO_4$, filtered and concentrated. The product was crystallized from hot EtOAc/hexanes providing the corresponding pyrimidine (520 mg) as a fluffy white powder. MS (ES+): 320.

Step 4

The hydroxy pyrimidine was covered with phosphorus oxychloride (5 ml) and stirred for 2 h. All volatiles were removed under vacuo. Toluene (20 ml) was added and then removed under vacuo (repeated once more). The residue was taken up in EtOAc (80 ml) and partitioned with an equal volume of 5% aqueous $NaHCO_3$. The organic phase was collected and washed with brine (80 ml). The aqueous phases were back-extracted with EtOAc (2×). The EtOAcphases were combined, dried over $MgSO_4$, filtered and stripped to provide the corresponding chloro pyrimidine (555 mg) as a tan-orange semi-viscous oil. MS (ES+): 338.

Step 5

To a mixture of the chloro pyrimidine (545 g, 1.6 mmol) and 1-methyl-(5-tributylstannyl)-imidazole (718 mg, 1.94 mmol) in dry benzene (20 mL) was added tetrakis (triphenylphosphine)-palladium(0) (60 mg). The mixture was refluxed for 5.5 h under argon. Additional 1-methyl-(5-tributylstannyl)-imidazole (350 mg) and palladium(0) catalyst (40 mg) were added and the mixture was heated for an additional 8 h. After cooling to ambient temperature the solvent was removed and the resultant material was purified by preparative TLC (MeOH/$CH_2Cl_2$ 1:9), which provided 6-diethoxymethyl-4-(1'-methyl-imidazole-5'-yl)-2-(4-methoxyphenylamino)-pyrimidine (649 mg) as a light yellow powder. MS (ES+): 384.

Step 6

The acetal (635 mg, 1.3 mmol) was covered with 3 $\underline{N}$ aqueous hydrochloric acid (25 ml) and heated to 50° C. After stirring for 2 h, the material was cooled to room temperature and all of the volatiles were removed under vacuo. The remainder was taken up in a mixture of EtOAc (80 mL) and 5% aqueous $NaHCO_3$ (80 ml) and stirred rapidly for about 5 minutes. The material was transferred to a separatory funnel and the organic phase was collected and washed with an equal volume of brine. The aqueous phases were back-extracted with EtOAc (2×80 mL), combined, dried over $MgSO_4$, filtered and concentrated to provide the corresponding aldehyde (465 mg) as an orange powder. MS (ES+): 310.

Step 7

To a solution of the aldehyde (100 mg, 0.323 mmol) in dry EtOH (10 ml) was added 2-methyl-3-thiosemicarbazide (34 mg, 0.323 mmol). The mixture was heated at reflux for 7 h. The reaction was cooled to room temperature and the volume concentrated by 50% under vacuo. The crystallized product was collected by filtration. The crystals were washed with ethanol (20 ml), followed by ethyl ether (20 ml), and dried under vacuum for 48 h to provide 2-(4-methoxy-phenylamino)-6-(1-methyl-3H-imidazol-5-yl)-pyrimidine-4-carbaldehyde 2-methyl-thiosemicarbazone. (93 mg); $^1$H-NMR (300 MHz, DMSO-$d_6$) 9.35 (s, 1H), 8.79 (s, 1H), 8.60 (s, 1H), 7.94 (d, 1H, J=1.0 Hz), 7.89 (s, 1H), 7.89 (s, 1), 7.80 (s, 1H), 7.62 (d, 2H, J=9.0 Hz), 7.52 (s, 1H,), 6.90 (d, 2H, J=9.0 Hz), 3.99 (s, 3H), 3.83 (s, 3H), 3.74 (s, 3H); MS (ES+): 397.

Procedure described in Example 2, step 1 through step 7 were followed, but 3,4-methylenedioxyanilinewas substituted for p-anisidine to provide 2-(3,4-methylenedioxyphenylamino)-6-(1-methyl-3H-imidazol-5-yl)-pyrimidine-4-carbaldehyde 2-methyl-thiosemicarbazone; $^1$H-NMR (300 MHz, DMSO-$d_6$) 9.41 (s, 1H), 8.79 (s, 1H), 8.60 (s, 1H), 7.95 (d, 1H, J=1.0 Hz), 7.91 (s, 1H), 7.81 (s, 1H,), 7.53 (s, 1H), 7.44 (s, 1H, br), 7.11–7.18 (m, 1H), 6.85 (d, 1H, J=8.4 Hz), 5.98 (s, 2H), 4.01 (s, 3H), 3.83 (s, 3H); MS (EI): ($M^+$) 411.

Example 3

Synthesis of 2-isopropylamino-6-thiazol-5-yl-pyrimidine-4-carbaldehyde 2-methyl-thiosemicarbazone

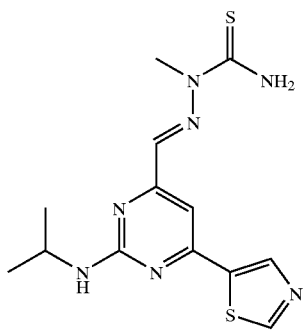

Step 1

A mixture of 2-benzylsulfanyl-4-Chloro-6-diethoxymethylpyrimidine (850 mg, 2.5 mmol), 2-trimethylsilyl-5-tributylstannylthiazole (2.0 g), and $PdCl_2(PPh_3)_2$ (200 mg) in DMF (6 ml) was heated at 80° C. After 3 h, the mixture was partitioned between EtOAc and water. The crude product was purified by prep TLC on silica gel (EtOAc/hexanes 1:2) to obtain the desired product (750 mg).

Step 2

The sulfide obtained above (750 mg) was dissolved in 40 ml of MeOH and treated with excess oxone (4.0 g) in 20 ml of water. The reaction mixture was stirred for 5 h at room temperature and then at 0° C. overnight. The mixture was partitioned between $CH_2Cl_2$ and water. The crude sulfone was dissolved in DMF (15 mL) and treated with isopropylamine (5 mL). After stirring overnight, the mixture was partitioned between EtOAc and water, the organics separeted and concentrated to dryness. The crude product was purified on prep TLC (EtOAc/hexane 1:1) to give the desired acetal pyrimidine (450 mg).

Step 3

The acetal (450 mg) was dissolved in 1:1 THF/3N HCl (30 ml) and heated at 50° C. for 5 h. The reaction mixture was poured into aqueous $NaHCO_3$ and the product was extracted with $CH_2Cl_2$, dried over $MgSO_4$, and concentrated to give an oil. The crude product was purified by prep TLC (EtOAc/hexane 1:1) to afford the desired aldehyde (260 mg).

Step 4

The aldehyde (130 mg) was suspended in EtOH (1 mL) and treated with 1.2 equivalents 2-methyl-3-thiosemicarbazide. After heating overnight at 80° C., in a sealed tube, the 2-isopropylamino-6-thiazol-5-yl-pyrimidine-4-carbaldehyde 2-methyl-thiosemicarbazone was filtered off and dried (61 mg) MS(ES+): 336.

Example 4

Synthesis of 6-imidazol-1-yl-2-isopropylamino-pyrimidine-4-carbaldehyde 2-methyl thiosemicarbazone.

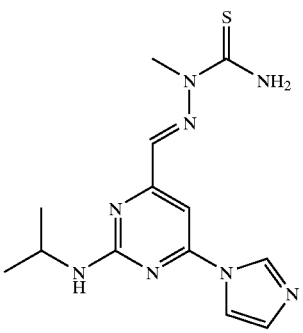

Step 1

A mixture of 2-benzylsulfanyl-4-Chloro-6-diethoxymethylpyrimidine (850 mg, 2.5 mmol) and imidazole (2 eq) was heated at 80° C. in DMF (4 ml) overnight. The mixture was partitioned between EtOAc and water. The organic layer separated, dried and concentrated to give the crude product (910 mg) The crude product was carried on to the next step.

Step 2

The sulfide (910 mg) was dissolved in MeOH (40 mL) and treated with excess oxone (4.0 g) in water (20 mL). After stirring at room temperature for 5 h, the reaction mixture was partitioned between $CH_2Cl_2$ and water. The crude sulfone was dissolved in DMF (15 mL) and treated with isopropylamine (5 mL). The reaction mixture was stirred overnight and then partitioned between EtOAc and water. The crude mixture was purified by prep TLC (EtOAc) to give 6-imidazol-1-yl-2-isopropylamino-pyrimidine-4-carbaldehyde diethylacetal (370 mg).

Step 3

The acetal (370 mg) was dissolved in 1:1 THF/3N HCl (30 mL) and heated at 50° C. for 5 h. The reaction mixture was poured into aqueous $NaHCO_3$ and the product was extracted with methylene chloride. The crude mixture was purified by prep TLC (EtOAc) to give the corresponding aldehyde(170 mg).

Step 4

The aldehyde (170 mg) was suspended in EtOH (1.5 mL) and treated with 1.25 equivalents 2-methyl-3-thiosemicarbazide. After heating overnight at 80° C., in a sealed tube, the desired product, 6-imidazol-1-yl-2-isopropylamino-pyrimidine-4-carbaldehyde 2-methyl thiosemicarbazone, was filtered off and dried(75 mg) MS(ES+):319.

Example 5

Synthesis of 2-isopropylamino-6-(4-methyl-4H-[1,2,4]triazol-3-yl)-pyrimidine-4-carbaldehyde 2-methyl thiosemicarbazone

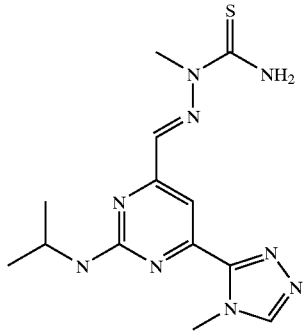

Step 1

2-benzylsulfanyl-4-Chloro-6-diethoxymethyl pyrimidine (5.0 g), 0.05 eq. of Pd(OAc)$_2$, 0.055 eq. of 1,3-bis(diphenylphosphino)-propane (DPPP) and 1.5 eq. of K$_2$CO$_3$ were charged to the flask containing n-propanol (54 mL) and DMF (27 mL). The flask was purged with N$_2$ following by CO (balloon). Reaction mixture was stirred at 90° C. under the CO atmosphere overnight. A solution of citric acid was added to the reaction mixture, stirred for 15 min and the product was extracted with EtOAc. Organic phase was dried over MgSO$_4$ and the solvent was removed in vacuum to afford the desired carboxylic acid (4.8 g, 93%). The material was used without purification.

Step 2

To a solution of the carboxylic acid (4.8 g) in 60 ml of MeOH/CH$_2$Cl$_2$ (2:1) was added of TMS diazomethane (21 mL) by portions at 0° C. The reaction mixture was stirred at 0° C. for 30 min after all of the reagent was added. Solvent was evaporated and the residue was purified on a silica gel column (EtOAc/hexane 2:98 to 8:92) to yield the corresponding ester (2.5 g, 50%) as a colorless oil.

Step 3

To a solution of the ester sulfide (2.5 g, 7 mmol) in 50 ml of MeOH was added a solution of oxone (13.0 g, 21 mmol) in water (100 mL). The reaction mixture was stirred at room temperature for 7 h. The reaction mixture was partitioned between CH$_2$Cl$_2$ and water. Organics were separated, dried over MgSO$_4$, and the solvent was removed under vacuum. The product (1.9 g, 70%) was used in the next reaction without purification.

Step 5

To a solution of the sulphone (1.9 g, 4.8 mmol) in THF (20 mL) was added isopropylamine (2.4 mL, 29 mmol). The reaction was stirred at room temperature overnight. The solvent was removed in vacuum. The residue was purified by column chromatography on silica gel (EtOAc/hexane 5:95) to give the desired ester (1.2 g 86%) as a clear oil.

Step 6

A mixture of the methyl ester (1.2 g) and LiOH (1.5 g) in 120 mL of MeOH/H$_2$O/THF (1:1:4) was stirred at 60° C. overnight. KOH (0.5 g) and 20 mL of THF were added and the reaction mixture was stirred at 60° C. for extra 48 h. The reaction mixture was poured on ice, acidified with acetic acid to pH 4.5–5 and extracted with CH$_2$Cl$_2$. The organic phase was dried over MgSO$_4$, the solvent was removed and the residue was dried on high vacuum to remove all acetic acid. The crude product was purified on prep. TLC (EtOAc/hexane 3:7) to give the carboxylic acid (500 mg) as an off-white solid.

Step 7

To a solution of the carboxylic acid (0.5 g, 1.8 mmol) in 30 mL of DMF were added 4-methyl-3-thiosemicarbazide (0.6 g, 5.4 mmol), HOBT (0.3 g, 2 mmol) and N-methylmorpholine (0.4 mL, 3.6 mmol). The mixture was cooled in ice-water bath and EDC (1.0 g, 5.4 mmol) was added to the reaction. The reaction mixture was stirred for 18 h at room temperature. DMF was removed under high vacuum, EtOAc was added to the flask and the solution was washed with 2.5N HCl (100 mL), brine (100 mL) and sat. NaHCO$_3$ (100 mL). The organic phase was dried over MgSO$_4$, and the solvent removed. The residue was purified on a prep TLC, (MeOH/CH$_2$Cl$_2$ 1:9) to give the desired product (0.51 g).

Step 8

Sodium metal (0.22 g) was dissolved in 10 mL of dry MeOH, the acyl semithiocarbazide (0.44 g, 1.2 mmol) was added and the reaction mixture was refluxed for 18 h under N$_2$. The reaction was cooled to room temperature, solvent was removed, the solids were dissolved in water and acidified with 10% HCl. The precipitate (0.12 g) was collected and the filtrate was purified on prep TLC (MeOH/CH$_2$Cl$_2$ 1:9) to obtain 0.05g of the desired 3-mercapto-1,2,4-triazole derivative (0.17 g, 42%).

Step 9

The mercapto triazole (0.17 g) was dissolved in 5 mL of EtOH, and Raney-Nickel (0.4 g washed several times with EtOH) added to the solution. The reaction mixture was refluxed for 18 h. The reaction was filtered through Celite, the solvent removed and the residue purified on prep TLC to give the corresponding acetal triazole (80 mg).

Step 10

To a solution of the acetal (80 mg) in 3 mL THF was added conc. HCl (3 mL) and refluxed for 18 h. The pH was adjusted to basic with aqueous NaHCO$_3$, and the aqueous phase extracted with CH$_2$Cl$_2$. Organic phase was dried over MgSO$_4$ and stripped. The residue was purified on prep. TLC (MeOH/CH$_2$Cl$_2$, 7:93) to give the corresponding aldehyde (40 mg, 66%).

Step 11

The aldehyde (40 mg) and 2-methyl-3-thiosemicarbazide (17 mg) in 1 mL of EtOH was stirred at reflux for 24 h. The precipitate was filtered off and dried under vacuum to give 2-isopropylamino-6-(4-methyl-4H-[1,2,4]triazol-3-yl)-pyrimidine-4-carbaldehyde 2-methyl thiosemicarbazone (36 mg, 67%). MS (ES+): 334

Example 6

Synthesis of 2-isopropylamino-6-(1-methyl-1H-imidazol-5-yl)-pyridine-4-carbaldehyde 2-methyl thiosemicarbazone

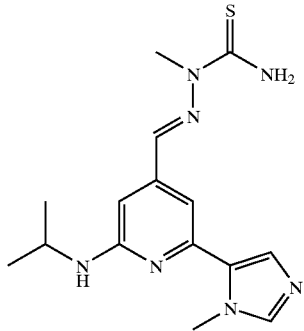

Step 1

To a solution of 2,6-dichloropyridine-4-carboxylic acid (8.28 g, 43.1 mmol, Aldrich) in dry THF (30 ml) was added N,N'-diisopropyl-O-t-butylisourea (17 ml, 3.6 M) dropwise over 1 minute. The resulting mixture was stirred at room temperature overnight. The material was then heated to 65° C. and additional N,N'-diisopropyl-O-t-butylisourea (10 ml) was added dropwise. The mixture was stirred for 1 hour and cooled to room temperature. After removing volatiles, the remainder was purified by flash silica gel column (EtOAc/hexanes 5:95 followed by 7.5:92.5)affording tert-butyl-2,6-dichloro-4-pyridine carboxylate (7.83 g, 73%) as a white solid. MS (ES+): 248.

Step 2

A mixture of tert-butyl 2,6-dichloro-4-pyridine carboxylate (1 g, 4.03 mmol) and isopropyl amine (3.4 ml, 40.3 mmol) in dry DMSO (5 mL) was heated, in a sealed tube, at 105° C. for 5 h. The mixture was cooled to room temperature and a solution of saturated ammonium chloride (30 ml) was added. The mixture was partitioned with EtOAc (40 mL) and the organic layer was collected and washed with an equal volume of brine. The aqueous phases were back extracted with EtOAc (2×30 ml), the organic phases combined, dried over $MgSO_4$ and filtered. The crude material was loaded onto a flash silica gel column (EtOAc/hexanes 1:9) to provided the corresponding chloro pyridine (820 mg) as a light yellow semi-viscous oil. MS (ES+): 271.

Step 3

To a mixture of the chloro pyridine (810 mg, 3.0 mmol) and 1-methyl-(5-tributylstannyl)-imidazole (1.3 g, 3.6 mmol) in dry benzene (20 mL) was added tetrakis(triphenylphosphine)-palladium(0) (150 mg). The mixture was refluxed for 18 h under argon. Additional 1-methyl-(5-tributylstannyl)-imidazole (1.4 g) and palladium(0) catalyst (150 mg) were added and the mixture was heated for an additional 5 h. After cooling to room temperature, the EtOAc 1.5:98.5) to afford the desired pyridine (1.21 g.) in approximately 50% purity. MS (ES+): 317.

Step 4

The pyridine ester (1.2 g, 50% pure, 1.9 mmol) was taken up in dry dioxane (20 ml). Sodium methoxide (1.02 g, 19 mmol) was added and the mixture was heated to 80° C. After 30 minutes additional sodium methoxide (1.02 g) was added and heating resumed for an additional 1.5 h. The mixture was cooled to room temperature, water (30 ml) was added, and the crude mixture was transferred to a separatory funnel. The aqueous phase was partitioned with ether (40 ml). The separated aqueous phase was condensed on the rotoevaporator, and traces of water were removed by azeotroping with toluene (2×60 ml), which afforded the corresponding crude sodiumpyridine carboxylate, which was not characterized but used directly in the next step.

Step 5

The crude sodium carboxylate (1.9 mmol) was taken up in dry methanol (30 ml) and concentrated sulfuric acid (3 ml) was added. The mixture was heated to reflux for 3 h and then cooled to room temperature. Approximately 90% of the methanol was removed (using the rotoevaporator); the remainder was taken up in water (45 ml) and partitioned with an equal volume of ether. Ether (45 mL) was added to the isolated aqueous phase and the mixture was brought to pH 9 by the addition of solid $Na_2CO_3$. EtOAc (20 ml) was added and the mixture was transferred to a separatory funnel. The organic phase was isolated and washed with an equal volume of water. The aqueous phases were back extracted with EtOAc (2×45 ml), the organic phases were combined, dried over $MgSO_4$, filtered, and concentrated to afford the corresponding methyl ester (402 mg) as a yellow-brown solid. MS (ES+): 275.

Step 6

The methyl ester (194 mg, 0.71 mmol) was taken up in dry THF(6 ml) and cooled to −78° C. (dry ice/acetone bath). Lithium aluminum hydride (1.1 ml, 0.95 M in THF) was added via syringe and the reaction mixture was allowed to warm to room temperature over 45 minutes. The reaction was quenched with acetic acid (10 drops, 50% in water) followed by saturated aqueous ammonium chloride (2 ml). The mixture was stirred for 20 minutes and then water (30 ml), saturated aqueous ammonium chloride (5 ml), and EtOAc(30 ml) were added and the material was transferred to a separatory funnel. The EtOAc phase was collected and washed with an equal volume of brine. The aqueous phases were back extracted with EtOAc (2×30 ml), combined, dried over $MgSO_4$, and concentrated the corresponding primary alcohol (167 mg) as a golden brown viscous oil. MS (ES+): 247.

Step 7

Dess-Martin periodinane (413 mg, 0.98 mmol) was taken up in dry $CH_2Cl_2$ (7 ml) and dry tert-butyl alcohol (0.1 ml, 1.35 mmol) was added. The mixture was stirred for 15 minutes and then added to a flask containing the alcohol (160 mg, 0.65 mmol) dissolved in $CH_2Cl_2$ (6 ml). The material was stirred for 30 minutes and then quenched by addition of aqueous 1 N sodium hydroxide (4.1 ml) followed by ethyl ether (20 ml). After stirring for 15 minutes, additional 1 N sodium hydroxide (4.3 ml) was added followed by ethyl ether (30 ml), water (50 ml), and EtOAc (10 ml). The material was transferred to a separatory funnel and the organic phase was collected and washed with an equal volume of 0.25 N aqueous sodium hydroxide, followed by water and brine. The aqueous phases were back extracted with a solution of 90% ethyl ether/EtOAc (2×60 ml) and the organic phases combined, dried over $MgSO_4$, filtered, and concentrated. The residue was purified by prep. TLC (MeOH/EtOAc 16:84) to afford the corresponding aldehyde (141 mg) as a yellow semi-solid. MS (ES+): 245.

Step 8

To a solution of the aldehyde (139 mg, 0.57 mmol) in dry ethanol (10 ml) was added 2-methyl-3-thiosemicarbazide (60 mg, 0.57 mmol) and the mixture was heated at reflux overnight. The reaction was cooled to room temperature and the volume was reduced by 50% on the rotoevaporator. Some crystals formed and were collected by filtration. The crystals were washed with ethanol (20 mL) followed by ethyl ether (20 mL) and then dried under vacuum for 48 h to provide 2-isopropylamino-6-(1-methyl-1H-imidazol-5-yl)-pyridine-4-carbaldehyde 2-methyl thiosemicarbazone (64 mg); $^1$H-NMR (300 MHz, DMSO-d$_6$) 8.57 (s, 1H), 8.32 (s, 1H), 7.71 (s, 1H), 7.65 (s, 1H), 7.53 (s, 1H), 7.40 (s, 1H), 6.63 (s, 1H), 6.51 (d, 1H, J=7.71 Hz), 3.98–4.15 (m, 1H), 3.96 (s, 3H), 3.78 (s, 3H), 1.18 (d, 6H, J=6.4 Hz); MS (ES+): 332.

Procedure described in Example 6, step 2 through step 8 were followed, but benzylamine was substituted for isopropylamine to provide 2-benzylamino-6-(1-methyl-1H-imidazol-5-yl)-pyridine-4-carbaldehyde 2-methyl thiosemicarbazone; $^1$H-NMR (300 MHz, DMSO-d$_6$) 8.58 (s, 1H), 8.34 (s, 1H), 7.74 (s, 1H), 7.59 (s, 1H), 7.52 (s, 1H), 7.46 (d, 1H, J=1 Hz), 7.18–7.36 (m, 6H), 6.76 (d, 1H, J=1 Hz), 4.56 (d, 1H, J=5.9 Hz), 3.78 (s, 3H), 3.73 (s, 3H); MS (EI): M$^+$ 380.

Example 7

Preparation of 2-(tetrahydropyran-4-ylmethyl)-4-trityl Thiosemicarbazide

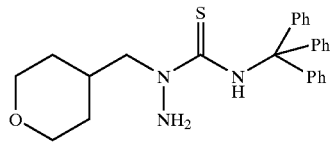

Step 1

To a solution of 4-hydroxymethyl tetrahydropyran (Radziszewski, J. G. et al, J. Amer. Chem. Soc.; 1993, 115, 8401) (7.55 g, 65 mmol) in CH$_2$Cl$_2$ (80 ml) at 0° C. was added Et$_3$N (11.5 ml, 83 mmol) followed by methanesulfonyl chloride (6.0 ml, 78 mmol). The reaction was stirred at 0° C. for 2 hr and then at room temperature for 1 h. The reaction diluted with CH$_2$Cl$_2$, washed with 10% NaHCO$_3$, water, brine, dried over Na$_2$SO$_4$ and concentrated to obtain the corresponding mesylate as a white solid (12.13 g).

Step 2

To a solution of the mesylate (12.13 g, 62.4 mmol) in ethanol (50 mL) was added hydrazine monohydrate (30 mL) and the mixture was heated to 60° C. for 2 h then concentrated to approx. 10 mL volume. Saturated aq. sodium hydroxide (20 mL) and THF (50 mL) were added and the organics collected, dried (NaSO$_4$), filtered and concentrated to afford and oil which was distilled (88–89° C., 2 mm/Hg) to give the desired hydrazine as a colorless liquid (5.7 g).

Step 3

To a stirred solution of the hydrazine (0.39 g, 3.0 mmol) in dry diethyl ether (20 mL) was added triphenylmethylisothiocyanate. The mixture was stirred at room temperature for 1 h and then the precipitate filtered to afford 2-(tetrahydropyran-4-ylmethyl)-4-trityl thiosemicarbazide as a white solid (1.0 g). $^1$H NMR (CDCl$_3$) δ 9.47(s, 1H), 7.17–7.36 (m, 15H), 3.92–4.03 (m, 4H), 3.83 (s, 2H), 3.37 (td, J=11.5, 2.5 Hz, 2H), 2.12 (m, 1H), 1.6–1.33 (m, 4H). MS (ES+): 432.

Example 8

Preparation of 2-(2-dimethyl ethyl)-4-trityl Thiosemicarbazide

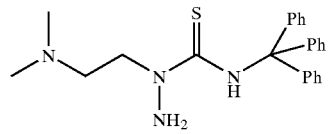

Step 1

A solution of NaOH (8.0 g, 0.2 mol) in hydrazine hydrate (25 ml) was heated to 95° C. The oil bath was removed and 2-dimethylaminoethylchloride hydrochloride (14.4 g, 0.1 mol) was added portionwise to keep the temperature at 95–100° C. The reaction was stirred at 95° C. for 1 h, the precipitate filtered and the residue distilled (73.5–74.5° C., 15–20 mm Hg) to give the corresponding alkyl hydrazine as a colorless liquid (3.8 g).

Step 2

To a solution of triphenylmethylisothiocyanate (3.0 g, 10 mmol) in ether (30 mL) was added the hydrazine (1.03 g, 10 mmol) at r.t. The reaction was stirred for 2 h at room temperature, the precipitate filtered to give 2-(2-dimethyl ethyl)-4-trityl thiosemicarbazide as a white solid (2.58 g). $^1$H NMR (CDCl$_3$) δ 9.64 (s, 1H), 7.12–7.37 (m, 15H), 4.71 (s, 1H), 4.15 (brt, J=5.1 Hz, 2H), 2.62 (brt, J=5.1 Hz, 2H), 2.26 (s, 6H). MS (ES+): 405.

Example 9

Preparation of 2-(2-hydroxy-2-methyl-but-4-yl)-4-trityl-thiosemicarbazide

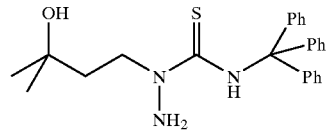

Step 1

To a solution of 3-methyl-1,3-butanediol (Fluka, 6.14 mL, 57.6 mmol) in DCM (20 mL) at 0° C. under an atmosphere of nitrogen was added triethylamine (10 mL). p-Toluenesulfonyl chloride (11 g) in DCM (20 mL) was added dropwise over 4 h and the mixture was stirred for a further 3 h at 0° C., then allowed to warm to room temperature overnight. The reaction mixture was diluted with water (50 mL) and the organics were separated, washed with 1M HCl (50 mL), sat. aq. NaHCO$_3$ (50 mL) and water (20 mL). The organics were dried (Na$_2$SO$_4$), filtered and concentrated to afford the corresponding tosylate (13.4 g, 90%) as a white solid. $^1$H NMR (CDCl$_3$) δ 7.81 (d, J=8 Hz, 2H), 7.37 (d, J=8 Hz, 2H), 4.22 (t, J=7 Hz, 2H), 2.47 (s, 3H), 1.88 (t, J=7 Hz, 2H), 1.23 (s, 6H).

Step 2

To a solution of the tosylate (6.55 g, 25 mmol) in ethanol (10 mL) was added hydrazine monohydrate (15 mL) and the mixture was heated to 60° C. for 2 h then concentrated to approx. 10 mL volume. Saturated aq. sodium hydroxide (20 mL) and THF (50 mL) were added and the organics collected, dried (NaSO$_4$), filtered and concentrated to afford the corresponding hydrazine (1.8 g, 60%) as a colorless oil. $^1$H NMR (CDCl$_3$) δ 4.73 (s, 1H), 3.19 (s, 3H), 3.02–3.06 (m, 2H), 1.68 (t, J=6 Hz, 2H), 1.26 (s, 6H). MS (ES+) 119.

Step 3

To a stirred solution of the hydrazine (0.8 g, 6.8 mmol) in dry diethyl ether (25 mL) was added triphenylmethylisothiocyanate (Trans World Chemicals, 1.83 g, 6.0 mmol). The mixture was stirred for 1 h and then hexanes (5 mL) was added and the mixture was filtered to afford 2-(2-hydroxy-2-methyl-but-4-yl)-4-trityl-thiosemicarbazide as a white solid (0.62 g, 22%). $^1$H NMR (CDCl$_3$) δ 9.49(s, 1H), 7.21–7.36 (m, 15H), 4.27 (t, J=6.3 Hz, 2H), 4.00 (s, 2H), 1.81 (t, J=6.6 Hz, 2H), 1.65 (s, 1H), 1.24 (s, 6H). MS (ES+): 420.

Example 10

Preparation of 2-(1-methanesulfonyl-piperidin-4-ylamino)-6-(1-methyl-1H-imidazol-5-yl)-pyrimidine-4-carbaldehyde 2-(2-hydroxy-2-methyl-but-4-yl)-thiosemicarbazone

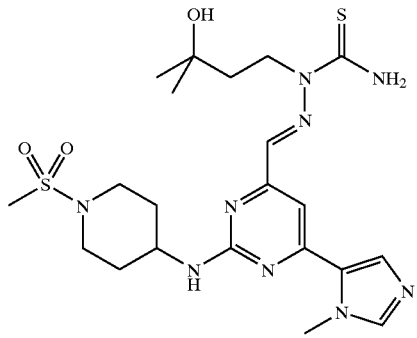

Step 1

A solution of the protected semithiocarbazide from Example 8 (70 mg, 0.16 mmol) in TFA:DCM/1:1 (2 ml) was stirred at room temperature for 1 h then concentrated in vacuo. Methanol (5 ml) was added and the mixture re-concentrated. This step was repeated 3 times until a white powder was obtained. Ethanol (3 ml) and 2-(1-methanesulfonyl-piperidin-4-ylamino)-6-(3-methyl-3-H-imidazol-4-yl)-pyrimidine-4-carbaldehyde (73 mg, 0.16 mmol) were added and the reaction mixture was stirred at 60° C. overnight, cooled to room temperature and precipitate filtered to obtain 2-(1-methanesulfonyl-piperidin-4-ylamino)-6-(1-methyl-1H-imidazol-5-yl)-pyrimidine-4-carbaldehyde 2-(2-hydroxy-2-methyl-but-4-yl)-thiosemicarbazone as a yellow solid (37.0 mg): mp 203.6–206.0° C.; $^1$H NMR (DMSO-d$_6$-D$_2$O) δ 8.66 (s, 1H), 8.18 (s, 1H), 7.63 (s, 1H), 7.60 (s, 1H), 4.52–4.62 (m, 2H), 4.14 (s, 3H), 3.89–4.00 (m, 1H)3.52–3.61 (m, 2H), 2.88–2.97 (m, 2H), 2.86 (s, 3H), 1.97–2.07 (m, 2H), 1.53–1.70 (m, 4H), 1.20 (s, 6H). MS (ES+): 524.

Compounds 11, 20, 21, 26, 28, 40, 74, 77, and 78 were prepared as described above in Example 10 with the corresponding protected thiosemicarbazide from Examples 7–9 and the corresponding aldehyde.

Example 11

Synthesis of 6-(4-acetonitrile-phenylamino)-2-(1-methyl-1H-imidazol-5-yl)-pyrimidine-4-carbaldehyde 2-methyl-thiosemicarbazone.

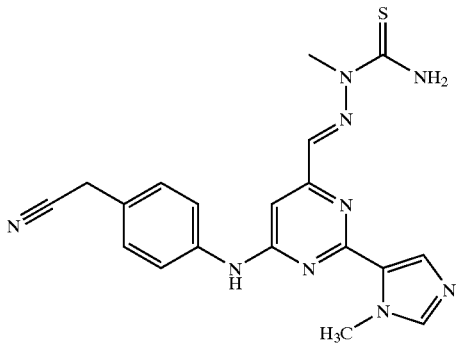

Step 1

To a solution of 2,6-dichloropyrimidine-4-carboxylate methyl ester (404 mg) in 10 mL of THF was added 4-aminophenyl acetonitrile and stirred at 60° C. under N$_2$ for 11 h. The solvent was removed in vacuum and the residue was purified on prep. TLC (hexanes/EtOAc, 9:1) to give the desired 6-substituted regioisomer (150 mg) along with the other isomer (100 mg).

Step 2

A solution of the 2-chloropyrimidine (0.53 g) and 1-methyl-5-tributyltin-imidazole (1.0 g) in 20 mL of dry DMF was purged with Ar for a few minutes. (PPh$_3$)$_2$Pd(II)Cl$_2$ (63 mg) was added and the reaction mixture was stirred at 80° C. for 24 h. The reaction mixture was poured into water and extracted with EtOAc (3×100 mL), the organic fraction was dried over MgSO$_4$ and the solvent was evaporated in vacuum. The crude product was purified on column (SiO$_2$, hexanes/EtOAc, 95:5) to give the desired 2-(imidazo-5-yl)-pyrimidine (0.22 g) as an oil.

Step 3

To a solution of the methyl ester (0.1 g, 0.3 mmol) in 5 mL of dry THF at −78° C. under N$_2$ was added a 1.0 M solution of LiAH$_4$ (0.32 mL) in THF. After stirring at this temperature for 30 min, more of the 1.0 M solution of LiAH$_4$ (0.15 ml) was added and 15 min later the reaction was quenched with saturated aqueous ammonium chloride. The reaction mixture was partitioned between water and EtOAc. The organic layer was dried over MgSO$_4$ and the solvent was removed in vacuum to yield a mixture of the corresponding alcohol and aldehyde (60 mg) which were separated on prep. TLC (CH$_2$Cl$_2$/MeOH, 95:5) to obtain the desired aldehyde (30 mg) in pure form.

Step 4

In a pressure tube were combined the aldehyde (30 mg) and 2-methyl-3-thiosemicarbazide (15 mg) in 1.0 mL of EtOH, capped and stirred at 80° C. for 24 h under Ar. The precipitate was filtered off, and dried in vacuum to give 6-(4-acetonitrile-phenylamino)-2-(1-methyl-1H-imidazol-5-yl)-pyrimidine-4-carbaldehyde 2-methyl-thiosemicarbazone (15 mg) as yellow crystals. MS (ES+): 406.

Example 12

The following compounds were all prepared by similar methods to those described in Examples 1–9.

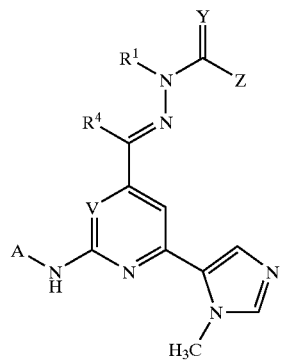

| A | V | R¹ | R⁴ | Y | Z | MS data (ES+) | Cpd No |
|---|---|---|---|---|---|---|---|
| $CH_3(CH_2)_3-$ | N | $CH_3$ | H | S | $NH_2$ | 347 | 1 |
| $CH_3-$ | N | $CH_3$ | H | S | $NH_2$ | 305 | 2 |
| $(CH_3)_2CH-$ | N | $CH_3$ | H | S | $NH_2$ | 333 | 3 |
| $PhCH_2-$ | N | $CH_3$ | H | S | $NH_2$ | 381 | 4 |
| cyclohexyl-CH₂- | N | $CH_3$ | H | S | $NH_2$ | 373 | 5 |
| (tetrahydrothiopyran-4-yl)-CH₂- | N | $CH_3$ | H | S | $NH_2$ | 391 | 6 |
| $PhH_2C-$N(piperidin-4-yl)-CH₂- | N | $CH_3$ | H | S | $NH_2$ | 464 | 7 |
| (tetrahydropyran-4-yl)-CH₂- | N | $CH_3$ | H | S | $NH_2$ | $NH_2$ (ES+) 375 | 8 |
| cyclopentyl-CH₂- | N | $CH_3$ | H | S | $NH_2$ | 359 | 9 |
| $PhCH_2CH_2-$ | N | $CH_3$ | H | S | $NH_2$ | 395 | 10 |
| $(CH_3)_2CH-$ | N | $(CH_3)_2N(CH_2)_2-$ | H | S | $NH_2$ | 391 | 11 |
| $Ph-$ | N | $CH_3$ | H | S | $NH_2$ | 367 | 12 |
| $HO-(CH_2)_2-$ | N | $CH_3$ | H | S | $NH_2$ | 335 | 13 |
| $PhCH_2-$ | CH | $CH_3$ | H | S | $NH_2$ | 380 | 14 |
| $(CH_3)_2CH-$ | CH | $CH_3$ | H | S | $NH_2$ | 332 | 15 |
| $(CH_3)_2CHCH_2-$ | N | $CH_3$ | H | S | $NH_2$ | 347 | 16 |
| cyclopropyl-CH₂CH₂- | N | $CH_3$ | H | S | $NH_2$ | 345 | 17 |
| (tetrahydrofuran-2-yl)-CH₂- | N | $CH_3$ | H | S | $NH_2$ | 375 | 18 |
| (pyridin-3-yl)-CH₂- | N | $CH_3$ | H | S | $NH_2$ | 382 | 19 |
| $PhCH_2-$ | N | $(CH_3)_2N(CH_2)_2-$ | H | S | $NH_2$ | 438 | 20 |

-continued

[Structure: pyrimidine core with substituents A-NH, V, and attached imidazole (N-methyl) and hydrazone-carboxamide side chain with R¹, R⁴, Y, Z]

| A | V | R¹ | R⁴ | Y | Z | MS data (ES+) | Cpd No |
|---|---|---|---|---|---|---|---|
| PhCH₂— | N | (tetrahydropyran-4-yl)CH₂— | H | S | NH₂ | 465 | 21 |
| H— | N | CH₃ | H | S | NH₂ | 291 | 22 |
| (4-pyridyl)CH₂CH₂— | N | CH₃ | H | S | NH₂ | 382 | 23 |
| cyclopropyl-CH₂— | N | CH₃ | H | S | NH₂ | 331 | 24 |
| (CH₃)₂CH— | N | H | H | O | NH₂ | 303 | 25 |
| (CH₃)₂CH— | N | (tetrahydropyran-4-yl)CH₂— | H | S | NH₂ | 417 | 26 |
| Ph— | N | H | H | O | NH₂ | 337 | 27 |
| Ph— | N | (tetrahydropyran-4-yl)CH₂— | H | S | NH₂ | 451 | 28 |
| (CH₃)₂CHCH₂CH(CH₃)— | N | CH₃ | H | S | NH₂ | 347 | 29 |
| (6-methyl-1,3-benzodioxol-5-yl)CH₂— | N | CH₃ | H | S | NH₂ | 411 | 30 |
| (4-MeO-phenyl)CH₂— | N | CH₃ | H | S | NH₂ | 397 | 31 |
| morpholino-(CH₂)₂— | N | CH₃ | H | S | NH₂ | 404 | 32 |
| morpholino-(CH₂)₃— | N | CH₃ | H | S | NH₂ | 418 | 33 |

-continued

| A | V | R¹ | R⁴ | Y | Z | MS data (ES+) | Cpd No |
|---|---|---|---|---|---|---|---|
| pyridin-2-yl-(CH₂)₂— | N | CH₃ | H | S | NH₂ | 396 | 34 |
| C₂H₅—O—C(O)—N(4-methylpiperidin-1-yl)— | N | CH₃ | H | S | NH₂ | 446 | 35 |
| NC-C₆H₄-(4-yl)— | N | CH₃ | H | S | NH₂ | 392 | 37 |
| NC-C₆H₄-(3-yl)— | N | CH₃ | H | S | NH₂ | 392 | 38 |
| NC-CH₂-C₆H₄-(4-yl)— | N | CH₃ | H | S | NH₂ | 406 | 39 |
| cyclopropyl— | N | tetrahydropyran-4-yl-CH₂— | H | S | NH₂ | 415 | 40 |
| Ac-N(4-methylpiperidin-1-yl)— | N | CH₃ | H | S | NH₂ | 416 | 41 |
| H₃C-S(O)₂-(CH₂)₃— | N | CH₃ | H | S | NH₂ | 411 | 42 |
| H₂N-C(O)-C₆H₄-(4-yl)-CH₂CH₂— | N | CH₃ | H | S | NH₂ | 424 | 43 |
| H₃C-S(O)₂-(CH₂)₂— | N | CH₃ | H | S | NH₂ | 397 | 44 |

-continued

| A | V | R¹ | R⁴ | Y | Z | MS data (ES+) | Cpd No |
|---|---|---|---|---|---|---|---|
| AcNH—⟨cyclohexyl⟩— | N | CH₃ | H | S | NH₂ | 430 | 45 |
| CH₃SO₂—N⟨piperidinyl⟩— | N | CH₃ | H | S | NH₂ | 452 | 46 |
| O₂N—⟨pyridinyl⟩—NH(CH₂)₂— | N | CH₃ | H | S | NH₂ | 456 | 47 |
| NC—⟨phenyl⟩— | N | CH₃ | H | S | NH₂ | 406 | 48 |
| HO—(CH₂)₅— | N | CH₃ | H | S | NH₂ | 377 | 49 |
| HO—(CH₂)₄— | N | CH₃ | H | S | NH₂ | 363 | 50 |
| CH₃SO₂—NH—⟨cyclohexyl⟩— | N | CH₃ | H | S | NH₂ | 466 | 51 |
| H₃CO—⟨phenyl⟩— | N | CH₃ | H | S | NH₂ | 397 | 52 |
| ⟨imidazolidinon-yl⟩—(CH₂)₂— | N | CH₃ | H | S | NH₂ | 403 | 53 |
| ⟨pyridin-3-yl⟩—(CH₂)₂— | N | CH₃ | H | S | NH₂ | 396 | 54 |
| NO₂—⟨phenyl⟩—(CH₂)₂— | N | CH₃ | H | S | NH₂ | 440 | 56 |

-continued
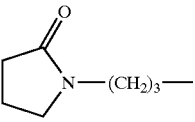
| A | V | R¹ | R⁴ | Y | Z | MS data (ES+) | Cpd No |
|---|---|---|---|---|---|---|---|
| 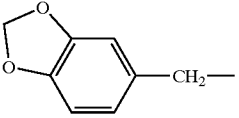 | N | CH₃ | H | S | NH₂ | 416 | 57 |
| 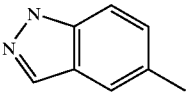 | N | CH₃ | H | S | NH₂ | 425 | 58 |
| (CH₃)₃C— | N | CH₃ | H | S | NH₂ | 347 | 59 |
| 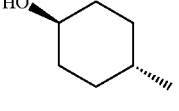 | N | CH₃ | H | S | NH₂ |  | 60 |
| 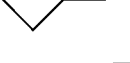 | N | CH₃ | H | S | NH₂ | 389 | 61 |
| 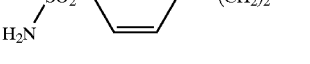 | N | CH₃ | H | S | NH₂ | 345 | 64 |
| 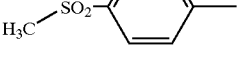 | N | CH₃ | H | S | NH₂ | 473 | 65 |
| 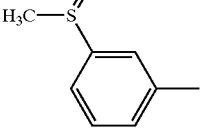 | N | CH₃ | H | S | NH₂ | 445 | 66 |
| 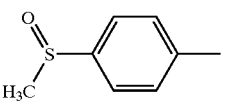 | N | CH₃ | H | S | NH₂ | 429 | 67 |
|  | N | CH₃ | H | S | NH₂ | 429 | 68 |

-continued
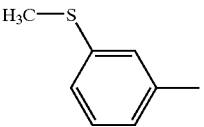
| A | V | R¹ | R⁴ | Y | Z | MS data (ES+) | Cpd No |
|---|---|---|---|---|---|---|---|
| 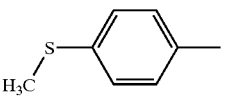 | N | CH₃ | H | S | NH₂ | 413 | 69 |
| 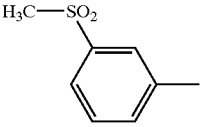 | N | CH₃ | H | S | NH₂ | 413 | 70 |
| 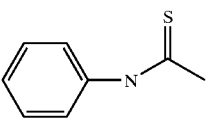 | N | CH₃ | H | S | NH₂ | 445 | 71 |
| 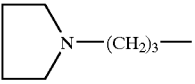 | N | CH₃ | H | S | NH₂ | 426 | 72 |
| 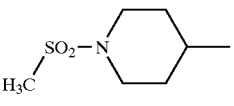 | N | CH₃ | H | S | NH₂ | 402 | 73 |
| 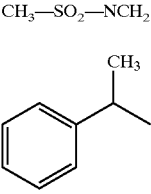 | N | 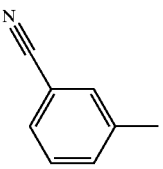 | H | S | NH₂ | 537 | 74 |
| CH₃—SO₂—NCH₂(CH₃)₂CCH₂— | N | CH₃ | H | S | NH₂ | 453 | 75 |
|  | N | CH₃ | H | S | NH₂ | 395 | 76 |
|  | N |  | H | S | NH₂ | | 77 |

-continued

| A | V | R¹ | R⁴ | Y | Z | MS data (ES+) | Cpd No |
|---|---|---|---|---|---|---|---|
| 6-methyl-benzo[1,3]dioxole | N | (tetrahydropyran-4-yl)CH₂— | H | S | NH₂ | 495 | 78 |
| 4-methyl-piperidine-1-carboxylic acid dimethylamide | N | CH₃ | H | S | NH₂ | 445 | 79 |
| CH₃—O—(CH₂)₂— | N | CH₃ | H | S | NH₂ | 347 | 80 |
| CH₃—O—(CH₂)₃— | N | CH₃ | H | S | NH₂ | 363 | 81 |
| (CH₃)₂CH—N—(O)C— | N | CH₃ | H | S | NH₂ | 376 | 82 |
| 1,1-dioxo-tetrahydrothiopyran-4-yl methyl | N | CH₃ | H | S | NH₂ | 423 | 83 |
| 3-(methylsulfonylamino)cyclohexyl | N | CH₃ | H | S | NH₂ | 466 | 84 |
| 6-methyl-1H-indazole | N | CH₃ | H | S | NH₂ | 407 | 85 |
| 4-(N,N-dimethylsulfamoyl)-piperidin-1-yl methyl | N | CH₃ | H | S | NH₂ | 481 | 86 |
| 4-(ethylsulfonyl)-piperidin-1-yl methyl | N | CH₃ | H | S | NH₂ | 466 | 87 |
| CH₃—S(O)₂—N(CH₂)₃— | N | CH₃ | H | S | NH₂ | 425 | 88 |
| CH₃—S(O)₂—N(CH₂)₄— | N | CH₃ | H | S | NH₂ | 440 | 89 |
| 4-(isopropylsulfonyl)-piperidin-1-yl methyl | N | CH₃ | H | S | NH₂ | 479 | 90 |

-continued

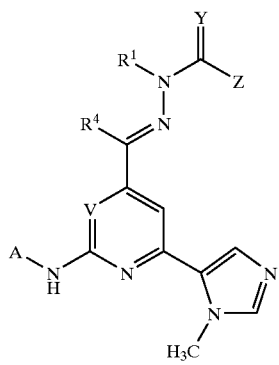

| A | V | R¹ | R⁴ | Y | Z | MS data (ES+) | Cpd No |
|---|---|---|---|---|---|---|---|
| ![] (O=C(CH₃)-(CH₂)₂-N-piperidine-4-CH₃) | N | $CH_3$ | H | S | $NH_2$ | 444 | 91 |
| ![] (O=C-N-piperidine-4-CH₃, connected via N) | N | $CH_3$ | H | S | $NH_2$ | 417 | 92 |
| $CH_3-S(O)_2-N-(CH_2)_2-$ | N | $CH_3$ | H | S | $NH_2$ | 412 | 93 |
| $(CH_3)_2CH-$ | N | H | $CH_3$ | S | $NH_2$ | 333 | 94 |
| ![] (O=C(CH₃)-CH₂-N-piperidine-4-CH₃) | N | $CH_3$ | H | S | $NH_2$ | 430 | 95 |
| ![] ($H_3C-SO_2-N$-piperidine-4-CH₃) | N | $HO(CH_3)_2C(CH_2)_2-$ | H | S | $NH_2$ | 524 | 96 |
| ![] (2,4-dimethoxyphenyl-CH₃) | N | $CH_3$ | H | S | $NH_2$ | 427 | 97 |
| $(CH_3)_2CH-$ | N | $CH_3$ | $CH_3$ | S | $NH_2$ | 347 | 98 |
| ![] ($H_2N-C(S)-N$-piperidine-4-CH₃) | N | $CH_3$ | H | S | $NH_2$ | 433 | 99 |
| ![] ($H_3C-NH-C(S)-N$-piperidine-4-CH₃) | N | $CH_3$ | H | S | $NH_2$ | 447 | 100 |
| ![] ($(H_3C)_2N-C(S)-N$-piperidine-4-CH₃) | N | $CH_3$ | H | S | $NH_2$ | 461 | 101 |

-continued

| A | V | R¹ | R⁴ | Y | Z | MS data (ES+) | Cpd No |
|---|---|---|---|---|---|---|---|
| N—SO₂—N(4-methylpiperidine)— | N | CH₃ | H | S | NH₂ | 453 | 102 |
| pyrazole-OH-(CH₂)₃— | N | CH₃ | H | S | NH₂ | | 103 |
| CH₃—C(O)—N—(CH₂)₃— | N | CH₃ | H | S | NH₂ | 390 | 104 |
| H₃C—SO₂—CH₂CH(CH₃)CH₂— (isopentyl sulfone) | N | CH₃ | H | S | NH₂ | 439 | 105 |
| H₃C—N(C=O)—(4-methylpiperidine)— | N | CH₃ | H | S | NH₂ | 431 | 106 |
| 2,3-dihydro-benzo[1,4]dioxin-6-yl— | N | CH₃ | H | S | NH₂ | 425 | 107 |
| Ph—SO₂—N—(CH₂)₃— | N | CH₃ | H | S | NH₂ | 488 | 108 |
| H₃C—NH—C(O)—NH—(4-methylphenyl)— | N | CH₃ | H | S | NH₂ | 439 | 109 |
| H₃C—SO₂—CH₂CH₂—N(4-methylpiperidine)— | N | CH₃ | H | S | NH₂ | 480 | 110 |
| NC—CH₂—N(piperidine)— | N | CH₃ | H | S | NH₂ | 431 | 111 |

-continued

| A | V | R¹ | R⁴ | Y | Z | MS data (ES+) | Cpd No |
|---|---|---|---|---|---|---|---|
| 2-methyl-6-methyl-benzothiazol-5-yl | N | CH₃ | H | S | NH₂ | 438 | 112 |
| 4-(methylsulfonylamino)-phenyl (methyl) | N | CH₃ | H | S | NH₂ | 460 | 113 |
| 5-methylpyridin-3-yl | N | CH₃ | H | S | NH₂ | 368 | 114 |
| 4-(methoxycarbonylamino)-3-methylphenyl | N | CH₃ | H | S | NH₂ | 440 | 115 |
| 3-(4-methylpiperidin-1-yl)propanenitrile | N | CH₃ | H | S | NH₂ | 427 | 116 |
| (1R,2S)-2-(hydroxymethyl)-2-methylcyclopropyl | N | CH₃ | H | S | NH₂ | 361 | 117 |
| 3-(methoxycarbonylamino)-4-methylphenyl | N | CH₃ | H | S | NH₂ | 440 | 118 |
| 3-(methylsulfonylamino)-4-methylphenyl | N | CH₃ | H | S | NH₂ | 460 | 119 |

-continued
| A | V | R¹ | R⁴ | Y | Z | MS data (ES+) | Cpd No |
|---|---|---|---|---|---|---|---|
|  | N | H | H | S | NHCH₃ | 333 | 120 |
|  | N | | H | S | N(CH₃)2 | 347 | 121 |
| 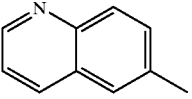 | N | | H | S | NH-n-C₄H₉ | 375 | 122 |
| 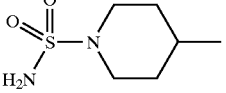 | N | CH₃ | H | S | NH₂ | 418 | 123 |
| 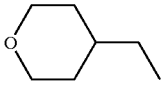 | N | 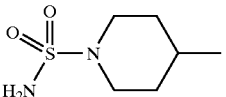 | H | S | NH₂ | 537 | 124 |
| 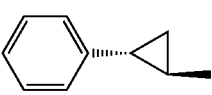 | N | n-C₄H₉ | H | S | NH₂ | 495 | 125 |
| 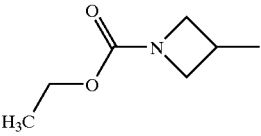 | N | CH₃ | H | S | NH₂ | 407 | 126 |
| 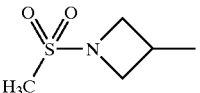 | N | CH₃ | H | S | NH₂ | 418 | 127 |
| | N | CH₃ | H | S | NH₂ | 424 | 128 |

-continued
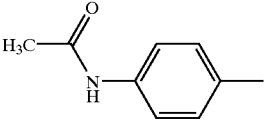
| A | V | R¹ | R⁴ | Y | Z | MS data (ES+) | Cpd No |
|---|---|---|---|---|---|---|---|
| 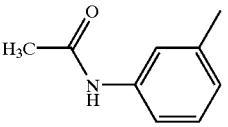 | N | CH₃ | H | S | NH₂ | 424 | 129 |
| 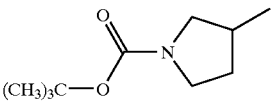 | N | CH₃ | H | S | NH₂ | 424 | 130 |
| 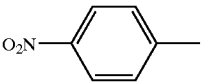 | N | CH₃ | H | S | NH₂ | 461 | 131 |
| 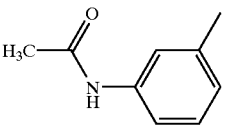 | N | CH₃ | H | S | NH₂ | 412 | 132 |
| 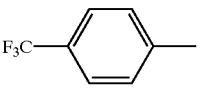 | N | CH₃ | H | S | NH₂ | 412 | 133 |
| 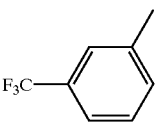 | N | CH₃ | H | S | NH₂ | 435 | 134 |
| 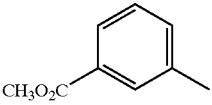 | N | CH₃ | H | S | NH₂ | 435 | 135 |
| 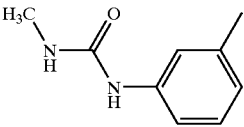 | N | CH₃ | H | S | NH₂ | 425 | 136 |
|  | N | CH₃ | H | S | NH₂ | 439 | 137 |

-continued

| A | V | R¹ | R⁴ | Y | Z | MS data (ES+) | Cpd No |
|---|---|----|----|----|----|----|----|
| (CH₃)₃CO-C(O)-N(piperidine-3-yl with methyl)- | N | CH₃ | H | S | NH₂ | 474 | 138 |
| CH₃-S(O)₂-N(pyrrolidine-3-yl with methyl)- | N | CH₃ | H | S | NH₂ | 438 | 139 |
| CH₃O₂C-C₆H₄- | N | CH₃ | H | S | NH₂ | 425 | 140 |
| HO-CH₂-C₆H₄- (meta) | N | CH₃ | H | S | NH₂ | 397 | 141 |
| HO-CH₂-C₆H₄- (para) | N | CH₃ | H | S | NH₂ | 397 | 142 |
| NC-CH₂-N(pyrrolidine-3-yl with methyl)- | N | CH₃ | H | S | NH₂ | 399 | 143 |
| CF₃-CH₂-CH₂- | N | CH₃ | H | S | NH₂ | 373 | 144 |
| H₂N-S(O)₂-N(pyrrolidine-3-yl with methyl)- | N | CH₃ | H | S | NH₂ | 439 | 145 |
| H₂N-C(O)-C₆H₄- | N | CH₃ | H | S | NH₂ | 410 | 146 |
| CH₃HN-C(O)-O-CH₂-C₆H₄- | N | CH₃ | H | S | NH₂ | 454 | 147 |

-continued

| A | V | R¹ | R⁴ | Y | Z | MS data (ES+) | Cpd No |
|---|---|---|---|---|---|---|---|
| 2-pyridyl-methyl | N | CH₃ | H | S | NH₂ | 368 | 148 |
| 4-(N-methylcarbamoyl)phenyl (CH₃HN-C(O)-C₆H₄-) | N | CH₃ | H | S | NH₂ | 424 | 149 |
| 2,3-dimethylphenyl | N | CH₃ | H | S | NH₂ | 395 | 150 |
| (2-cyanomethyl-cyclopropyl) | N | CH₃ | H | S | NH₂ | 370 | 151 |
| 1-methylcyclopropyl | N | CH₃ | H | S | NH₂ | 345 | 152 |
| 4-(thiocarbamoyl)phenyl | N | CH₃ | H | S | NH₂ | 426 | 153 |
| 3-acetylphenyl | N | CH₃ | H | S | NH₂ | 409 | 154 |
| 3-(1-hydroxyethyl)phenyl | N | CH₃ | H | S | NH₂ | 411 | 155 |

| | | | | | | MS data (ES+) | Cpd No |
|---|---|---|---|---|---|---|---|
| A | V | R¹ | R⁴ | Y | Z | | |
| H₃C-C(=O)-C₆H₄-CH₃ | N | CH₃ | H | S | NH₂ | 409 | 156 |
| H₃C-N(OCH₃)-C(=O)-C₆H₄-CH₃ | N | CH₃ | H | S | NH₂ | 454 | 157 |
The following compounds have also been prepared:
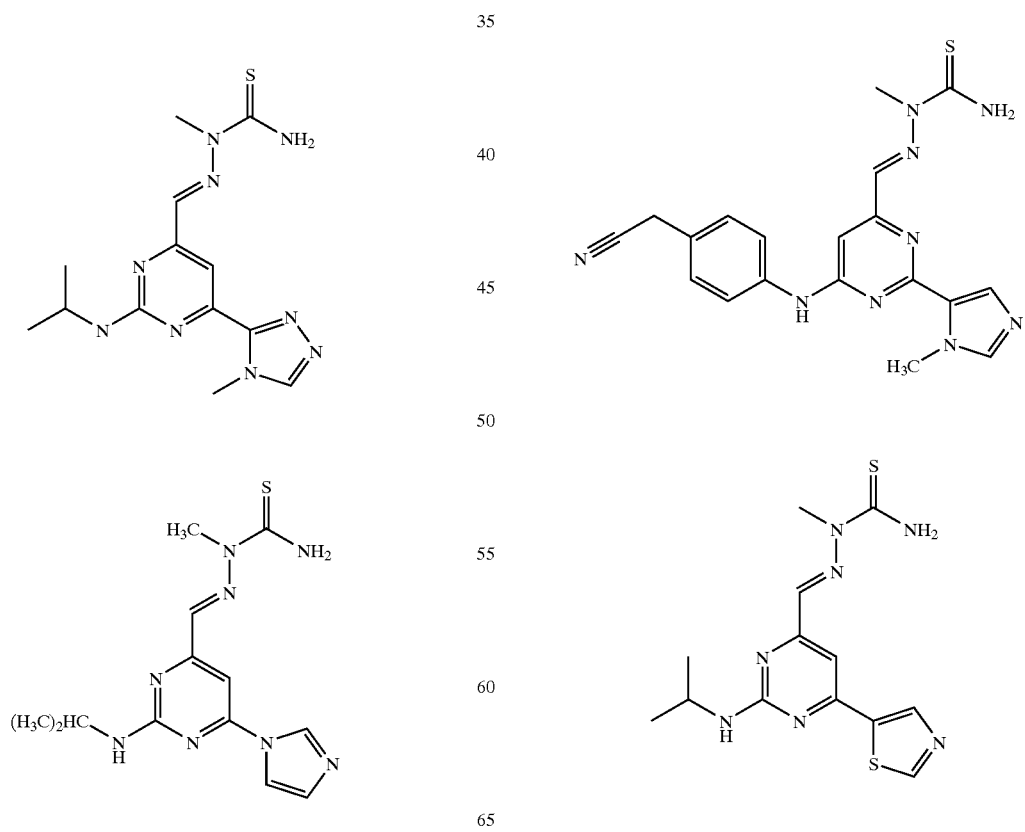

Example 13

This example provides an assay that is useful in evaluating and selecting a compound that modulates IKK-β kinase.

Assay Protocol for Measuring IKKβ Enzyme Inhibition 96 well polystyrene microtiter plates were coated with Neutravidin (10 μg/mL in PBS, overnight at 4° C.). The coating solution was removed and in 80 μl/well a kinase reaction mixture was added (20 mM Tris-HCl, pH 7.5, 10 mM MgCl$_2$, 2 mM EGTA, 1 mM NaF, 0.5 mM benzamidine, 1 mM DTT, 0.1% NP-40, 10 μM ATP, 1 μM of biotinylated substrate peptide KKERLLDDRHDSGLDSMKDEEYEQGK-bio, sequence derived from IκB-alpha). In 10 μl/well in DMSO test compounds were added covering a final concentration range from 1 nM to 30 μM. Recombinant full-length IKKβ enzyme was added in 10 μl buffer containing Tris-HCl pH 7.5 20 mM, EGTA 2 mM, benzamidine 0.5 mM, DTT 1 mM, NP-40 0.1%, MgCl$_2$ 10 mM to initiate the kinase reaction. The reaction mixture was incubated at room temperature for 45 min. During this incubation the substrate peptide gets phosphorylated by IKKβ and gets captured onto the well's surface by Neutravidin. The plate was washed 3× with 150 μl distilled water to terminate the reaction and remove components of the reaction mixture.

A conventional chemiluminescent ELISA detection technique was initiated by adding 100 μl/well primary antibody (custom-made monoclonal antibody generated to recognize the phosphorylated epitope in the substrate peptide; used at 1:10,000 dilution) premixed with horseradish peroxidase (HRP) conjugated anti-mouse secondary antibody (commercially available from several sources; used at 1:10,000 dilution) in PBS containing 2% BSA. The solution was incubated at room temperature for 40 min on a shaker, then washed 3× with 150 μl of water. 100 μl/well 10× diluted SuperSignal HRP substrate (from Pierce) was added and after 5 min incubation the chemiluminescent signal was captured by a Labsystems LuminoSkan luminometer. The point of 50% inhibition of IKKβ enzyme activity (IC50) was determined by curve fitting with the LSW data analysis software (MDL, San Leandro, Calif.).

The compounds provided in Examples 1–5 and 9–11 displayed IC$_{50}$ values of less than or equal to about 60 μM in the above assay.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:
1. A compound having the formula:

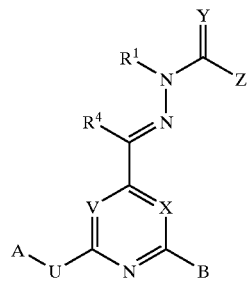

wherein
one of either V or X is N and the other is —CR$_a$, or both V and X are —CR$_a$ (where each R$_a$ is independently hydrogen, alkyl, cycloalkyl or cycloalkylalkyl;
Y is selected from the group consisting of O, S and NR;
wherein R is selected from the group consisting of H, CN, NO$_2$, (C$_1$–C$_{10}$)alkyl, (C$_3$–C$_7$)cycloalkyl, (C$_3$–C$_7$)cycloalkyl-alkyl, (C$_3$–C$_{10}$)alkenyl and (C$_2$–C$_{10}$)alkynyl;
Z is selected from the group consisting of H, (C$_1$–C$_6$)alkyl, (C$_3$–C$_7$)cycloalkyl, (C$_3$–C$_6$)cycloalkyl-alkyl, (C$_2$–C$_6$)alkenyl, (C$_2$–C$_6$)alkynyl and N(R$^2$)(R$^3$);
R$^1$ is selected from the group consisting of H, (C$_1$–C$_{10}$)alkyl, (C$_3$–C$_{10}$)alkenyl, (C$_2$–C$_{10}$)alkynyl, (C$_3$–C$_7$)cycloalkyl, (C$_3$–C$_7$)cycloalkyl-alkyl, (C$_1$–C$_{10}$)heteroalkyl, heterocyclyl, heterocyclylalkyl, aryl, aryl(C$_1$–C$_4$)alkyl, aryl(C$_1$–C$_4$)heteroalkyl, heteroaryl(C$_1$–C$_4$)alkyl, heteroaryl(C$_1$–C$_4$)heteroalkyl, —C(O)R$^{11}$ and alkylene-C(O)R$^{11}$;
R$^{11}$ is hydrogen, (C$_1$–C$_6$)alkyl or NR$^{12}$R$^{13}$ (where R$^{12}$ and R$^{13}$ are independently hydrogen, (C$_1$–C$_6$)alkyl or heteroalkyl);
R$^2$ and R$^3$ are each members independently selected from the group consisting of H, (C$_1$–C$_{10}$)alkyl, (C$_3$–C$_{10}$)alkenyl, (C$_2$–C$_{10}$)alkynyl, (C$_3$–C$_7$)cycloalkyl, (C$_3$–C$_7$)cycloalkyl-alkyl and (C$_1$–C$_{10}$)heteroalkyl, or R$^2$ and R$^3$ can be combined to form a 5–7-membered heterocyclyl ring;
R$^4$ is selected from the group consisting of H, (C$_1$–C$_6$)alkyl, (C$_3$–C$_7$)cycloalkyl, (C$_3$–C$_7$)cycloalkyl-alkyl, (C$_2$–C$_6$)alkenyl and (C$_2$–C$_6$)alkynyl;
A is selected from the group consisting of H, (C$_1$–C$_{10}$)alkyl, (C$_1$–C$_{10}$)haloalkyl, (C$_3$–C$_{10}$)alkenyl, (C$_2$–C$_{10}$)alkynyl, (C$_3$–C$_7$)cycloalkyl, (C$_3$–C$_7$)cycloalkyl-alkyl, (C$_1$–C$_{10}$)heteroalkyl, heterocyclyl, heterocyclylalkyl, heterosubstituted cycloalkyl, aryl, aryl(C$_1$–C$_4$)alkyl, aryl(C$_1$–C$_4$)heteroalkyl, heteroaryl, heteroaryl(C$_1$–C$_4$)alkyl, heteroaryl(C$_1$–C$_4$)heteroalkyl and R$^a$NHC(=X)— wherein R$^a$ is (C$_1$–C$_4$)alkyl or aryl and X is O or S;
B is a substituted or unsubstituted five- or six-membered aromatic ring containing at least one nitrogen atom, and from 0 to 3 additional heteroatoms, wherein the B ring substituents are selected from the group consisting of halogen, CF$_3$, CF$_3$O, (C$_1$–C$_6$)alkyl, amino, (C$_1$–C$_6$)alkylamino, di(C$_1$–C$_6$)alkylamino, cyano, nitro, sulfonamido, acyl, acylamino and carboxamido;
U is NR$^5$, O or S; and,
R$^5$ is H or (C$_1$–C$_6$)alkyl.
2. The compound of claim 1, wherein V is N and X is CH.
3. The compound of claim 2, wherein Y is selected from the group consisting of O and S.

4. The compound of claim 3, wherein $R^4$ is H.

5. The compound of claim 4, wherein B contains a nitrogen atom at a position two atoms away from the atom attaching B to the remainder of the molecule.

6. The compound of claim 5, wherein B is selected from the group consisting of substituted or unsubstituted imidazolyl, substituted or unsubstituted thiazolyl and substituted or unsubstituted triazolyl.

7. The compound of claim 6, wherein B is selected from the group consisting of 1-methylimidazol-5-yl, 1-(trifluoromethyl)imidazol-5-yl, 5-methylimidazol-1-yl, 5-(trifluoromethyl)imidazol-1-yl, thiazol-5-yl, imidazol-1-yl and 4-methyl-1,2,4-triazol-3-yl.

8. The compound of claim 6, wherein U is NH.

9. The compound of claim 8, wherein Z is $N(R^2)(R^3)$.

10. The compound of claim 9, wherein Z is $NH_2$.

11. The compound of claim 10, wherein Y is S.

12. The compound of claim 11, wherein $R^1$ is selected from the group consisting of $(C_1-C_{10})$alkyl, $(C_1-C_{10})$heteroalkyl, heterocyclylalkyl, heteroaryl$(C_1-C_4)$alkyl and alkylene-C(O)$R^{11}$.

13. The compound of claim 12, wherein A is selected from the group consisting of $(C_1-C_{10})$alkyl, $(C_3-C_7)$cycloalkyl, $(C_1-C_{10})$heteroalkyl, heterocyclyl, heterocyclylalkyl, heterosubstituted cycloalkyl, aryl, aryl$(C_1-C_4)$alkyl and heteroaryl.

14. The compound of claim 4, wherein $R^1$ is selected from the group consisting of $(C_1-C_{10})$alkyl, $(C_1-C_{10})$heteroalkyl, heterocyclylalkyl, heteroaryl$(C_1-C_4)$alkyl and alkylene-C(O)$R^{11}$.

15. The compound of claim 14, wherein B contains a nitrogen atom at a position two atoms away from the atom attaching B to the remainder of the molecule.

16. The compound of claim 15, wherein B is selected from the group consisting of substituted or unsubstituted imidazolyl, substituted or unsubstituted thiazolyl and substituted or unsubstituted triazolyl.

17. The compound of claim 16, wherein B is selected from the group consisting of 1-methylimidazol-5-yl, 1-(trifluoromethyl)imidazol-5-yl, 5-methylimidazol-1-yl, 5-(trifluoromethyl)imidazol-1-yl, thiazol-5-yl, imidazol-1-yl and 4-methyl-1,2,4-triazol-3-yl.

18. The compound of claim 16, wherein U is NH.

19. The compound of claim 18, wherein Z is $N(R^2)(R^3)$.

20. The compound of claim 4, wherein Z is $NH_2$.

21. The compound of claim 20, wherein A is selected from the group consisting of $(C_1-C_{10})$alkyl, $(C_3-C_7)$cycloalkyl, $(C_1-C_{10})$heteroalkyl, heterocyclyl, heterocyclylalkyl, heterosubstituted cycloalkyl, aryl, aryl$(C_1-C_4)$alkyl and heteroaryl.

22. The compound of claim 21, wherein $R^1$ is selected from the group consisting of $(C_1-C_{10})$alkyl, $(C_1-C_{10})$heteroalkyl, heterocyclylalkyl, heteroaryl$(C_1-C_4)$alkyl and alkylene-C(O)$R^{11}$.

23. The compound of claim 22, wherein B contains a nitrogen atom at a position two atoms away from the atom attaching B to the remainder of the molecule.

24. The compound of claim 23, wherein B is selected from the group consisting of substituted or unsubstituted imidazolyl, substituted or unsubstituted thiazolyl and substituted or unsubstituted triazolyl.

25. The compound of claim 24, wherein B is selected from the group consisting. of 1-methylimidazol-5-yl, 1-(trifluoromethyl)imidazol-5-yl, 5-methylimidazol-1-yl, 5-(trifluoromethyl)imidazol-1-yl, thiazol-5-yl, imidazol-1-yl and 4-methyl-1,2,4-triazol-3-yl.

26. The compound of claim 24, wherein U is NH.

27. The compound of claim 1, wherein V is CH and X is N.

28. The compound of claim 27, wherein Y is O or S; Z is $NH_2$; and U is NH.

29. The compound of claim 28, wherein A is selected from the group consisting of $(C_1-C_{10})$alkyl, $(C_3-C_7)$cycloalkyl, $(C_1-C_{10})$heteroalkyl, heterocyclyl, heterocyclylalkyl, heterosubstituted cycloalkyl, aryl, aryl$(C_1-C_4)$alkyl and heteroaryl.

30. The compound of claim 29, wherein $R^1$ is selected from the group consisting of $(C_1-C_{10})$alkyl, $(C_1-C_{10})$heteroalkyl, heterocyclylalkyl, heteroaryl$(C_1-C_4)$alkyl and alkylene-C(O)$R^{11}$.

31. The compound of claim 30, wherein B contains a nitrogen atom at a position two atoms away from the atom attaching B to the remainder of the molecule.

32. The compound of claim 31, wherein B is selected from the group consisting of substituted or unsubstituted imidazolyl, substituted or unsubstituted thiazolyl and substituted or unsubstituted triazolyl.

33. A composition comprising a pharmaceutically acceptable excipient and a compound of claim 1.

34. The composition of claim 33, wherein V is N and X is CH.

35. The composition of claim 34, wherein Y is selected from the group consisting of O and S.

36. The composition of claim 35, wherein $R^4$ is H.

37. The composition of claim 36, wherein B contains a nitrogen atom at a position two atoms away from the atom attaching B to the remainder of the molecule.

38. The composition of claim 37, wherein B is selected from the group consisting of substituted or unsubstituted imidazoyl, substituted or unsubstituted thiazolyl and substituted or unsubstituted triazolyl.

39. The composition of claim 38, wherein Z is $NH_2$.

40. The composition of claim 39, wherein $R^1$ is selected from the group consisting of $(C_1-C_{10})$alkyl, $(C_1-C_{10})$heteroalkyl, heterocyclylalkyl, heteroaryl$(C_1-C_4)$alkyl and alkylene-C(O)$R^{11}$.

41. The composition of claim 40 wherein A is selected from the group consisting of $(C_1-C_{10})$alkyl, $(C_3-C_7)$cycloalkyl, $(C_1-C_{10})$heteroalkyl, heterocyclyl, heterocyclylalkyl, heterosubstituted cycloalkyl, aryl, aryl$(C_1-C_4)$alkyl and heteroaryl.

42. A method of treating an inflammatory, metabolic or malignant condition, said method comprising administering to a subject in need of such treatment, an effective amount of a compound of claim 1.

43. The method of claim 42, wherein V is N and X is CH.

44. The method of claim 43, wherein the compound is administered orally.

45. The method of claim 43, wherein the compound is administered topically.

46. The method of claim 43, wherein the compound is administered intravenously or intramuscularly.

47. The method of claim 43, wherein the compound is administered in combination with a second therapeutic agent, and wherein the second therapeutic agent is selected from the group consisting of prednisone, dexamethasone, beclosmethasone, methylprednisone, betamethasone, hydrocortisone, methotrexate, cyclosporin, rapamycin, tacrolimus, antihistamine drugs, TNF antibodies, IL-1 antibodies, soluble TNF receptors, soluble IL-1 receptors, TNF or IL-1 receptor antagonists, non-steroidal anti-inflammatory agents, COX-2 inhibitors, antidiabetic agents and anticancer agents.

48. The method of claim 43, wherein the administering is sequential.

49. The method of claim 43, wherein the inflammatory, metabolic or malignant condition is selected from the group consisting of rheumatoid arthritis, inflammatory bowel disease, psoriasis, cancer, diabetes and septic shock.

50. A method for the preparation of anti-inflammation agents comprising contacting a precursor compound having the formula:

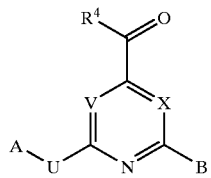

wherein
one of either V or X is N and the other is —$CR_a$, or both V and X are —$CR_a$ (where each $R_a$ is independently hydrogen, alkyl, cycloalkyl or cycloalkylalkyl;

$R^4$ is selected from the group consisting of H, $(C_1–C_6)$ alkyl, $(C_3–C_7)$cycloalkyl, $(C_3–C_7)$cycloalkyl-alkyl, $(C_2–C_6)$alkenyl and $(C_2–C_6)$alkynyl;

A is selected from the group consisting of H, $(C_1–C_{10})$ alkyl, $(C_1–C_{10})$haloalkyl, $(C_3–C_{10})$alkenyl, $(C_2–C_{10})$ alkynyl, $(C_3–C_7)$cycloalkyl, $(C_3–C_7)$cycloalkyl-alkyl, $(C_1–C_{10})$heteroalkyl, heterocyclylalkyl, heterocyclyl, heterosubstituted cycloalkyl, aryl, aryl$(C_1–C_4)$alkyl, aryl$(C_1–C_4)$heteroalkyl, heteroaryl, heteroaryl$(C_1–C_4)$ alkyl, heteroaryl$(C_1–C_4)$heteroalkyl and $R^aNHC$ (=X)— wherein $R^a$ is $(C_1–C_4)$alkyl or aryl and X is O or S;

B is a substituted or unsubstituted five- or six-membered aromatic ring containing at least one nitrogen atom, and from 0 to 3 additional heteroatoms, wherein the B ring substituents are selected from the group consisting of halogen, $CF_3$, $CF_3O$, $(C_1–C_6)$alkyl, amino, $(C_1–C_6)$ alkylamino, di$(C_1–C_6)$alkylamino, cyano, nitro, sulfonamido, acyl, acylamino and carboxamido;

U is $NR^5$, O or S; and,
$R^5$ is H or $(C_1–C_6)$alkyl with a compound having the formula:

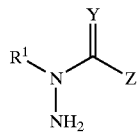

wherein
Y is selected from the group consisting of O, S and NR; wherein R is selected from the group consisting of H, CN, $NO_2$, $(C_1–C_{10})$alkyl, $(C_3–C_7)$cycloalkyl, $(C_3–C_7)$cycloalkyl-alkyl, $(C_3–C_{10})$alkenyl and $(C_2–C_{10})$alkynyl;

Z is selected from the group consisting of H, $(C_1–C_6)$ alkyl, $(C_3–C_7)$cycloalkyl, $(C_3–C_7)$cycloalkyl-alkyl, $(C_2–C_6)$alkenyl, $(C_2–C_6)$alkynyl and $N(R^2)(R^3)$;

$R^1$ is selected from the group consisting of H, $(C_1–C_{10})$ alkyl, $(C_3–C_{10})$alkenyl, $(C_2–C_{10})$alkynyl, $(C_3–C_7)$ cycloalkyl, $(C_3–C_7)$cycloalkyl-alkyl, $(C_1–C_{10})$ heteroalkyl, heterocyclylalkyl, heterocyclyl, aryl, aryl$(C_1–C_4)$alkyl, aryl$(C_1–C_4)$heteroalkyl, heteroaryl$(C_1–C_4)$alkyl, heteroaryl$(C_1–C_4)$ heteroalkyl, —$C(O)R^{11}$ or alkylene-$C(O)R^{11}$; and $R^2$ and $R^3$ are each members independently selected from the group consisting of H, $(C_1–C_{10})$alkyl, $(C_3–C_{10})$alkenyl, $(C_2–C_{10})$alkynyl, $(C_1–C_{10})$ heteroalkyl, $(C_3–C_7)$cycloalkyl, or $(C_3–C_7)$ cycloalkyl-alkyl, or $R^2$ and $R^3$ can be combined to form a 5–7-membered heterocyclyl ring;

under conditions sufficient to produce compounds having the formula:

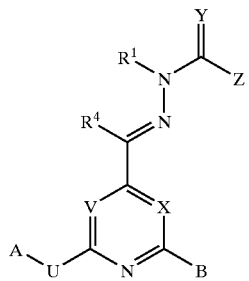

wherein each of A, B, $R^1$, $R^4$, U, V, X Y and Z have the meanings provided above.

51. The method of claim 50, wherein:

V is N and X is CH;
Y is O or S;
Z is $NH_2$;
$R^1$ is is selected from the group consisting of $(C_1–C_{10})$ alkyl, $(C_1–C_{10})$heteroalkyl, heterocyclylalkyl, heteroaryl$(C_1–C_4)$alkyl and alkylene-$C(O)R^{11}$;
$R^4$ is H;
A is selected from the group consisting of $(C_1–C_{10})$alkyl, $(C_3–C_7)$cycloalkyl, $(C_1–C_{10})$heteroalkyl, heterocyclyl, heterocyclylalkyl, heterosubstituted cycloalkyl, aryl, aryl$(C_1–C_4)$alkyl and heteroaryl;
B is is selected from the group consisting of substituted or unsubstituted imidazoyl, substituted or unsubstituted thiazolyl and substituted or unsubstituted triazolyl; and
U is NH.

* * * * *